(12) United States Patent
Morris et al.

(10) Patent No.: US 8,486,451 B2
(45) Date of Patent: Jul. 16, 2013

(54) ADSORPTION AND RELEASE OF NITRIC OXIDE IN METAL ORGANIC FRAMEWORKS

(75) Inventors: Russell Edward Morris, St. Andrews (GB); Paul Stewart Wheatley, St. Andrews (GB)

(73) Assignee: The University Court of the University of St. Andrews, St. Andrews (GB)

( * ) Notice: Subject to any disclaimer, the term of this patent is extended or adjusted under 35 U.S.C. 154(b) by 631 days.

(21) Appl. No.: 12/377,429

(22) PCT Filed: Aug. 16, 2007

(86) PCT No.: PCT/GB2007/003129
§ 371 (c)(1),
(2), (4) Date: Jun. 9, 2010

(87) PCT Pub. No.: WO2008/020218
PCT Pub. Date: Feb. 21, 2008

(65) Prior Publication Data
US 2010/0239512 A1    Sep. 23, 2010

(30) Foreign Application Priority Data
Aug. 17, 2006  (GB) .................................. 0616350.5

(51) Int. Cl.
| A61K 33/00 | (2006.01) |
| A61K 8/19 | (2006.01) |
| C07F 1/08 | (2006.01) |
| C07F 19/00 | (2006.01) |
| A61P 17/00 | (2006.01) |
| A61P 31/10 | (2006.01) |
| A61P 31/12 | (2006.01) |
| A61P 31/04 | (2006.01) |
| A61P 35/00 | (2006.01) |
| A61P 17/06 | (2006.01) |
| A61Q 15/00 | (2006.01) |
| A61Q 19/08 | (2006.01) |

(52) U.S. Cl.
USPC ................. 424/465; 556/112; 556/58; 546/2; 424/718; 424/73; 424/70.1

(58) Field of Classification Search
None
See application file for complete search history.

(56) References Cited

U.S. PATENT DOCUMENTS
| 6,624,318 B1 * | 9/2003 | Muller et al. ................. 549/529 |
| 7,652,132 B2 * | 1/2010 | Yaghi et al. ................... 540/145 |
| 2004/0037836 A1 * | 2/2004 | Stamler et al. ............ 424/178.1 |
| 2006/0185388 A1 * | 8/2006 | Muller et al. ................... 62/606 |

FOREIGN PATENT DOCUMENTS
| WO | WO 03/101975 A1 | 12/2003 |
| WO | WO 2004/002611 A1 | 1/2004 |
| WO | WO 2004/037895 A1 | 5/2004 |
| WO | WO 2005/003032 A1 | 1/2005 |

OTHER PUBLICATIONS

Padden et al. Immobilized Metal Complexes in Porous Organic Hosts: Development of a Material for the Selective and Reversible Binding of Nitric Oxide. J. Am. Chem. Soc. 2001, pp. 1072-1079.*
Cho et al. "A metal-organic framework material that functions as an enantioselective catalyst for olefin epoxidation", Chemical Communications 24:2563-2565 (2006).
DeRosa et al. "Chemical pretreatment of olive oil mill wastewater using a metal-organic framework catalyst", J. Agricultural and Food Chem. 53(21):8306-8561 (2005).
Evanhoe "Catalyst in a cage", Chemical and Eng. News 84(26):38-39 (2006).
Fujita et al. "Preparation clathration ability and catalysis of a 2D square network material composed of cadminum (II) and 4,4'-bipyridine", J. Am. Chemical Soc. 116:1151-1152 (1994).
Hill et al. "New complexes and materials for 02-based oxidations", J. Molecular Catalysis 251(1-2):234-238 (2006).
Naito et al. "A Novel Reaction Pathway in Olefin-Deuterium Exchange Reaction inside the Micropores of Rh(II) Dicarboxylate Polymer Complexes", Chemistry Letters 30(11):1178-1179 (2001).
Ohmura et al. "Magnetic and Gas-Occlusion Properties and Catalytic Activity of Microporous Materials: Dinuclear Ruthenium (II, II) Dicarboxylates", Chemistry Letters 32(5):468-469 (2003).
Schlichte et al. "Improved synthesis, thermal stability and catalytic properties of the metal-organic framework compound Cu3(BTC)2", Microporous and Mesoporous Materials 73(1-2):81-88 (2004).
Wheatley et al. "NO-releasing zeolites and their antithrombotic properties", J. Am. Chemical Soc. 128)2):502-509 (2006).
Xiao et al. "High-capactiy hydrogen and nitric oxide adsorption and storage in a metal-organic framework", J. Am. Chemical Soc. 129(5):1203-1209 (2007).
Notification of Transmittal of the International Search Report and the Written Opinion of the International Searching Authority, or the Declaration corresponding to International Application No. PCT/GB2007/003129 mailed Dec. 28, 2007.
Written Opinion of the International Searching Authority corresponding to International Application No. PCT/GB2007/003129 mailed Dec. 28, 2007.
Notification of Transmittal of the International Preliminary Report on Patentability corresponding to International Application No. PCT/GB2007/003129 mailed Oct. 24, 2008.
Ignarro et al., "Nitric oxide donors and cardiovascular agents modulating the bioactivity of nitric oxide", Circ. Res., vol. 90, pp. 21-28 (2002).

(Continued)

Primary Examiner — Scott Long
Assistant Examiner — Sarah Alawadi
(74) Attorney, Agent, or Firm — Susan T. Evans; McDermott Will & Emery LLP

(57) ABSTRACT

Disclosed are metal organic frameworks that adsorb nitric oxide, NO-loaded metal organic frameworks, methods of preparing the NO-loaded metal organic frameworks, methods of releasing the nitric oxide into a solution or into air, and uses of the metal organic frameworks.

28 Claims, 23 Drawing Sheets

OTHER PUBLICATIONS

Rowsell and Yaghi, "Metal-organic frameworks: a new class of porous materials," Micro. Meso. Mat., vol. 73, pp. 3-14 (2004).

Ohrström, Lars, "Terminology for Coordination Polymers and MOFs", ChemViews Magazine, pp. 1-2 (2013).

* cited by examiner

ADSORPTION AND RELEASE OF NITRIC OXIDE IN METAL ORGANIC FRAMEWORKS

FIELD OF INVENTION

The present invention relates to metal organic frameworks that adsorb nitric oxide, NO-loaded metal organic frameworks, methods of preparing the NO-loaded metal organic frameworks, methods of releasing the nitric oxide into a solution or into air, and uses thereof.

BACKGROUND OF THE INVENTION

Nitric oxide (the chemical formula is NO) is a remarkable small molecule that is vitally important in many biological processes. It is a vasodilator that increases blood flow through arteries and veins, and is also an important factor in controlling platelet adhesion and aggregation. It also plays a crucial role in the immune system. Much is now known about the mode of action of nitric oxide and it is clear that it has enormous potential in medicine and biotechnology in both in vivo and ex vivo applications.

The controlled delivery of nitric oxide may be important in therapy. For example, nitric oxide can prevent thrombosis and restenosis following balloon angioplasty and stent insertion in blocked arteries (International Patent Application WO 95/24908). The delivery of nitric oxide to the skin may also have therapeutic benefits for patients with peripheral circulatory problems which can occur in conditions such as arthritis and Raynaud's syndrome. Nitric oxide also plays a part in wound healing and angiogenesis, and delivery of nitric oxide to wounds can be beneficial when healing is slow which can occur, for example, in elderly patients (M. Shabani et al, Enhancement of wound repair with a topically applied nitric oxide-releasing polymer *Wound repair and regeneration*, 4, 353, 1996 and S. Frank H. Kampfer, C. Wetzler, J. Pfeilschifer, Nitric oxide drives skin repair: Novel functions of an established mediator *Kidney International*, 61, 882, 2002).

However the delivery of nitric oxide to the desired area, and in the required optimum dose is often difficult because nitric oxide is a gas. Delivery of nitric oxide is difficult in both ex vivo e.g. biotechnology applications and in vivo e.g. medical applications.

Various methods of nitric oxide delivery are known such as
(a) molecules which release NO spontaneously;
(b) molecules which are metabolised to give NO;
(c) molecules that release NO on photoactivation;
(d) release of NO from polymers and polymer coatings;
(e) Release of NO from zeolites
(f) production of NO from a chemical reaction.

The class (a) molecules are known as nitric oxide nucleophile complexes (NONOates) (C. M. Maragos et al, Complexes of NO with nucleophiles as agents for the controlled biological release of nitric-oxide-vasorelaxant effects *J. Med. Chem.*, 34, 3242, 1991). These are a variety of molecules which give off nitric oxide spontaneously and have been shown to have a possible use in therapeutic applications (U.S. Pat. No. 4,954,526). However the use of NONOates in therapy is limited because they become distributed throughout the body which may compromise selectivity. The by-products following the release of NO may also form carcinogenic secondary nitrosamines.

The class (b) molecules include glyceryl trinitrate and sodium nitroprusside (L. J. Ignarro Biosynthesis and metabolism of endothelium-derived nitric-oxide *Ann. Rev. Pharmacol. Toxicol.* 30, 535, 1990). These compounds are currently widely used as vasodilators, however prolonged use can lead to toxic side products such as cyanides. Furthermore, because these molecules need to be metabolised to release NO, the targeting of NO to particular sites may also be poor resulting in the effects tending to be systemic.

The class (c) molecules require specific activation, for example, light having a specific wavelength which can be difficult to initiate (C. Works, C. J. Jocher, G. D. Bart, X. Bu, P. C. Ford, Photochemical Nitric Oxide Precursors *Inorg. Chem.*, 41, 3728, 2002).

Class (d) release of nitric oxide mitigates the problems associated with systemic activity by delivering nitric oxide to a specific target site by supporting a nitric oxide releasing compound on a solid article. Such NO releasing compounds may be polymeric materials which can be coated onto medical instruments which can be used to target specific areas of the body for treatment. The polymers may contain, for example, the $N_2O_2$ group that releases NO after a chemical reaction (International Patent Application WO 95/24908 and US Patent Application 2002094985). However, the release of NO in such circumstances can be difficult to control and currently the preparation of the required materials may be expensive. The possible use of such polymers has been shown in the treatment of cardiovascular problems, for example, restenosis.

Class (e) also mitigates the problems associated with systemic activity by releasing the nitric oxide from a crystalline metal-exchanged porous aluminosilicate porous framework material called a zeolite (International patent application WO 2005/003032 (2005)). The reported capacity of these materials is acceptable at about 1 mmol of NO per g of zeolite and the materials have been shown to have anti-thromobosis properties (Wheatley et al. Journal of the American Chemical Society, 128, 502-509, 2006,)

Class (f) delivery of nitric oxide has been proposed for topical applications by releasing nitric oxide from a chemical reaction. The chemical reaction involves the application of sodium nitrite, ascorbic acid and maleic acid, which gives off NO when contacted by water (U.S. Pat. No. 6,103,275). However, this reaction takes place only in acidic conditions and produces a number of side products, some of which are unidentified, and so may cause irritation, especially to sensitive skin of elderly patients.

Nitric oxide is also an important pollutant molecule and therefore there is a need for the removal of this gas from car exhausts and from waste gas streams. High adsorption capacities are necessary for the materials to work well in these applications also.

Thus, there is a need for means which enable the adsorption and storage of nitric oxide, particularly high capacity storage of nitic oxide, and which may facilitate the subsequent release of nitric oxide when release/delivery is required.

Metal-organic frameworks (MOFs) are a class of nanoporous material. In these solids metal ions ($M^{n+}$) are linked together with organic units ($L^{y-}$) to form three dimensional networks. Many of these networks show good thermal stability and are extremely porous, with up to ~90% free volume. (O. M. Yaghi et al. *Nature*, 423, 705, 2003 (b) H. Li et al *Nature* 402, 276, 1999. (c) WO200288148-A).

Yaghi and co-workers (M. Eddouadi et al, *Science* 295, 469, 2002) have reported some storage capacities of up to 240 $cm^3$ of methane per gram of MOF (equivalent to >10 mmol per g). Results have been reported for the storage of hydrogen by MOFs (Rosi et al. *Science*, 300, 1127, 2003). Metal organic frameworks have been reported as useful gas storage materials (WO2003064030-A, WO2005049484-A1) and as catalysts (US2004081611-A1, WO2004099148-A1).

The use of these MOFs for nitric oxide adsorption, storage and release and the provision of further MOFs for those purposes is not described.

The object of the present invention is to obviate and/or mitigate the problems of nitric oxide adsorption, storage and delivery.

SUMMARY OF THE INVENTION

According to a first aspect of the present invention, there is provided a metal organic framework comprising material, which comprises adsorbed nitric oxide.

Metal organic frameworks (MOFs) are a class of nanoporous material. In these solids the metal ions ($M^{n+}$) are linked together with linkers ($L^{y-}$) to form three dimensional networks.

In metal organic frameworks the metals may comprise any of a number of metal cations, such as transition metal cations, alkali metal cations, alkaline earth metal cations and other suitable metal cations, such as for example aluminium cations.

For example, suitable transition metal cations may include one or more of the following: $Ti^{n+}$, $V^{n+}$, $Cr^{n+}$, $Mn^{n+}$, $Fe^{n+}$, $Co^{n+}$, $Ni^{n+}$, $Cu^{n+}$, $Zn^{n+}$, $Ag^{n+}$, $Ru^{n+}$, $Rh^{n+}$ where n is 1, 2, 3 or 4, depending on the metal and the oxidation state of that metal.

Suitable transition metal cations include $Cu^+$, $Cu^{2+}$, $Mn^{2+}$, $Mn^{3+}$, $Zn^{2+}$, $Fe^{2+}$, $Fe^{3+}$, $V^{3+}$, $V^{4+}$, $Ag^+$, $Ru^{3+}$, $Rh^{3+}$, $Ni^{2+}$, $Cr^{2+}$, $Co^{2+}$ and $Co^{3+}$.

Suitable alkali metal cations include $Na^+$ and $K^+$.

Suitable alkaline earth metal cations include $Ca^{2+}$ and $Mg^{2+}$.

Other metal cations include for example $Al^{3+}$.

Transition metal cations are preferred, for example preferred metal cations may be selected from $Cu^+$, $Cu^{2+}$, $Cr^{2+}$, $Zn^{2+}$, $Fe^{2+}$, $Fe^{3+}$, $Co^{2+}$, $Co^{3+}$, $Ag^+$, $Mn^{2+}$ and $Mn^{3+}$.

The metal organic framework may comprise any one or more than one of the above listed types of metal cations together in the same framework material.

Mixtures of more than one type of organic framework material may also be provided.

For biological, medical and/or cosmetic applications (see herein below), preferred metal cations are those which are deemed toxicologically acceptable for such uses, e.g. those metals which are considered to have acceptable/limited toxicity, particularly when presented in the framework material, although such considerations will depend on the circumstances of the use and may be determined by the skilled practitioner as appropriate.

The ligand linkers (L) may comprise organic compounds (i.e based on carbon) containing multiple coordinating atoms or functional groups.

For example, each ligand may include 2-10 coordinating sites, e.g. 2-6 coordinating sites, most preferably 2-4 coordinating sites, for example 2 or 3 coordinating sites.

The coordinating sites may provide an electron donating moiety, e.g. a lone pair of electrons, a negative charge, or atoms or groups capable of forming such moieties.

Typically, each ligand is a dentate ligand, for example a bidentate, tridentate or other multiple-dentate ligand.

Preferred ligands include carboxylate ligands, for example, 1,4-benzenedicarboxylic acid, 1,3,5-benzene tricarboxylic acid, sulfoisophthalic acid (e.g. 5-sulfoisophthalic acid or other isomers thereof e.g. 4-sulfoisophthalic acid) or the like, each of which is presented as the carboxylate ion species in the framework.

Other preferred ligands include amines, for example, 1,4-bipyridine or the like.

The metal-organic frameworks may comprise or contain additional entities to those described above, for example, further metal or other positively charged ions, or other anionic species.

Further anions may include halogens, e.g. $Cl^-$, $F^-$, $Br^-$ or $I^-$ or other anions, e.g. $OH^-$ or $SO_4^-$.

The metal organic frameworks may in particular include species/molecules, within guest sites, such as pores or channels, formed in the framework. Such species may be for example water, solvent or other molecules e.g. derived from the components used in the manufacture of the framework.

According to a second aspect of the present invention, there is provided a method of preparing a metal organic material which comprises releasably adsorbed nitric oxide, said method comprising the steps of providing said metal organic material and contacting said metal organic material with nitric oxide gas.

Prior to nitric oxide adsorption (loading), the metal organic frameworks for use in the present invention may (or may not) be fully or partially activated. The term 'activated' refers to the metal organic framework being presented in a state in which nitric oxide may be adsorbed at least 'irreversibly' to some degree. The frameworks may inherently allow the nitric oxide to be adsorbed irreversibly (at least to some extent), in which case, activation may not be required, or activation may be used to increase the amount of nitric oxide which may be adsorbed.

If required, activation generally involves the removal of guest molecules/species from the interior of the pores and/or channels of the framework to allow the nitric oxide to be adsorbed into the metal organic framework. The guest molecules/species may be coordinated to the metals in the metal organic framework, and the activation of the framework materials may include removal of such coordinated molecules/species. The guest molecules/species may be nuleophiles.

For example, the metal organic framework may become coordinatively activated, wherein the activated metal organic framework includes a site available for coordination on some or all of the metal cations that form part of the framework itself. The available metal cations are thus available to strongly ('irreversibly') bind nitric oxide through coordination of the gas to the metal cation(s).

Therefore, as a preferment, the metal organic framework comprising material comprises at least some irreversibly adsorbed nitric oxide.

The term 'irreversible' adsorption of nitric oxide refers to nitric oxide which is bound to the metal organic framework stongly and is not substantially desorbed from the material once the nitric oxide-containing atmosphere used to load the material with the gas is removed, in particular, at a reduced pressure. Without wishing to be bound by theory, this irreversible adsorption is understood to be a chemisorption process (i.e. there is a chemical bond formed between the nitric oxide and the metal organic framework material). The presence of irreversibly adsorbed nitric oxide (or any other species) is indicated by a strong hysteresis between the adsorption and desorption arms of the adsorption/desorption isotherm.

In contrast, reversibly adsorbed nitric oxide is weakly bound to the material and desorbs once the nitric oxide-containing atmosphere used to load the material with the gas is removed. The nitric oxide adsorbed by this mechanism is thereby termed 'reversibly' bound nitric oxide.

Activation may be achieved chemically, optionally followed by other non-chemical means or vice versa.

Chemical activation tends to remove the unwanted guest molecules from the framework by chemical displacement of the guest molecules by the molecules of the chosen activating chemical species. The nitric oxide itself may be used to displace the unwanted guest molecules.

The other, non-chemical, means for activation may include heating the metal organic framework at ambient (e.g. atmospheric) or reduced pressure. Subjecting the framework material to reduced pressure in absence of heat may also be used. Methods include, for example, placing the framework under vacuum at elevated temperatures.

Other, non-chemical means for activation include exposing the metal organic framework to electromagnetic radiation, e.g. ultraviolet light.

Preferably, the framework is subjected to a chemical activation procedure followed by heating. Such method advantageously may take advantage of a step-wise activation procedure whereby guest molecules/species are preferentially displaced by a different chemical entity which becomes a guest molecule/species, which is then removed from the framework under reduced pressure and/or heating the framework material.

Chemical activation may be achieved using a chemical treatment method such as exposure of the framework material to a desired chemical or a mixture of chemicals.

Examples of suitable chemicals include solvents such as acetonitrile ($CH_3CN$), dimethylformamide (DMF), ethanol (EtOH) or methanol (MeOH).

Typical pressures, preferably reduced pressures, which may be used for activation include a pressure less than atmospheric pressure, e.g. less than 1 bar, such as from about $1 \times 10^{-4}$ mbar to about 1 bar.

Typical temperatures, preferably elevated temperatures, which may be used for activation include a temperature up to about 450° C., for example, from about 20° C. to about 250° C., preferably, about 50° C. to about 150° C., most preferably about 80° C. to about 120° C., e.g. about 110° C.

The guest molecules may comprise water, in which case, activation of the framework includes full or partial dehydration of the framework material, to remove water. Other guest molecules such as residual solvent or gases may also be removed from the metal organic framework by the activation methods described herein.

The activation of the metal organic frameworks may also involve a change in structure of the framework to enable nitric oxide to be adsorbed irreversibly.

The resulting metal organic framework may then be exposed to nitric oxide to load the metal organic framework.

Typically, the nitric oxide loading is performed at a temperature of from −100° C. to 50° C.

The loading of nitric oxide may be performed with pure NO, substantially pure NO or with a mixture of NO and a carrier gas such as an inert gas, for example helium, argon or other inert gas including mixtures thereof.

The loading is typically performed at a pressure above atmospheric pressure, for example from atmospheric pressure up to a pressure of about 10 bar. Atmospheric pressure is generally understood to mean a pressure of about 1 bar.

The nitric oxide loaded metal organic frameworks may be sealed inside airtight packaging for storage and transport purposes.

The airtight packaging may conveniently contain a dry atmosphere under which the metal organic framework is sealed.

Upon exposure of the nitric oxide loaded metal organic framework to a suitable nucleophile, for example an aqueous environment such as water or blood: the nitric oxide is displaced from the metal complex inside the metal organic framework resulting in release of nitric oxide gas into the aqueous environment.

Thus, the irreversibly adsorbed nitric oxide may be considered to be releasably adsorbed nitric oxide when conditions under which its release is triggered are applied.

The release of the irreversibly adsorbed/bound nitric oxide may be triggered by the action of another species, e.g. one which preferentially becomes the guest in the metal organic framework, for example, displaces and takes the place of the nitric oxide at the coordination sphere of the metal cation in the metal organic framework. Such species include, for example, nucleophile species, and the method of release may comprise using a nucleophile-containing medium such as moist gas or an aqueous medium/solution, or by other means such as subjecting the nitric oxide-containing material to an elevated temperature or exposure to electromagnetic radiation, e.g. ultraviolet light.

The nitric oxide loaded material may be subjected to one or more these methods to render the irreversibly bound nitric oxide releasable, prior to subjecting the material to conditions to actually release the irreversibly bound nitric oxide.

The nitric oxide may be released from the nitric oxide loaded metal organic framework when placed in air, e.g. moist air.

The release of nitric oxide may occur at a variety of temperatures, however room temperature (about 25° C.) or body temperature (about 38° C.) is preferred.

Metal organic framework materials, including those described herein, especially when activated as described herein, irreversibly adsorb a high capacity of nitric oxide, making the materials particularly suitable for nitric oxide adsorption, storage and/or release.

Typically, more than about 7 mmol, e.g. up to about 5 mmol of nitric oxide per gram of the metal organic framework may be adsorbed, and this corresponds to greater than three times the adsorption capacity of other known porous materials such as zeolites. The amount adsorbed may however be less, such as up to 3 mmol or 4 mmol, e.g. up to about 1.5 mmol or 2.0 mmol nitric oxide per gram of the metal organic framework. Thus, a range of about 1 mmol to 7 mmol may be envisaged.

Ideally, the organic metal framework should have a high capacity for irreversibly adsorbed nitric oxide, for example, substantially all of the initially loaded nitric oxide is irreversibly adsorbed, i.e. the material loading capacity should have as high as possible ratio of irreversible to reversible nitric oxide.

Preferably, the amount of irreversibly adsorbed nitric oxide is about 1.0 mmol, or greater, per gram of metal organic framework material. For example, the amount of irreversibly adsorbed nitric oxide is from about 1.0 mmol per gram to about 6.0 mmol per gram, e.g. from 1.0 mmol per gram to about 4.0 mmol per gram.

Typically, the mole ratio value of irreversible to reversible nitric oxide is from about 2 to about 7, e.g. from about 2.5 to about 6, e.g. about 3.5. As mentioned above, higher ratios are preferred.

The precise amounts of nitric oxide measured in calculating the indicated ratios depends at least partially on the measurement conditions such as adsorption/desorption temperature and pressure. Generally, an isotherm gragh may be generated for measurement purposes, showing adsorption and desorption arms, spanning a pressure of from about zero (e.g. about $1 \times 10^{-2}$ mbar) to about 1000 mbar (atmospheric pressure) at 298K (about room temperature), with the amounts of nitric oxide for calculation purposes each being recorded at about zero pressure. Thus, as an example, at room temperature, at the start of the measurement at the starting zero pressure, the amount of nitric oxide adsorbed in a chosen metal organic framework material is zero, rising to e.g. about 1.75 mmol NO per gram at 1000 mbar, and reducing to about 1.25 mmol per gram on reducing the pressure to zero again. That is, 0.5 mmol per gram of NO is reversibly adsorbed. The residual 1.25 mmol per gram of NO is the irreversibly adsorbed nitric oxide, and the ratio between the irreversible to reversible NO is 1.25/0.5=2.5.

The nitric oxide loaded metal organic framework may be prepared in the form of a powder or a monolith for use for example in topical therapeutic applications or for ex vivo uses such as in vitro applications such as delivery of specific amounts of NO to cell cultures. For example, a specific amount of NO may be loaded into a metal organic framework and then, knowing the extent of release or release profile of the NO loaded metal organic framework, a precise amount of NO may be delivered to the cell culture. This principle may also be applied to other delivery applications of NO e.g. in therapeutic applications so that a specific amount or dose of NO may be administered.

The monoliths May be formed by compression of a metal organic framework powder or by mixing a powdered metal organic framework with a suitable binder which is well known in the manufacture of metal organic framework catalysts.

Suitable binders include, but are not limited to, ceramic binders, e.g. silica or alumina, and polymeric binders, e.g. polysulfone, polyethane, PET, polystyrene, polytetrafluorethylene (PTFE) and other polymers.

Alternatively the metal organic frameworks may be provided as coatings on medical devices such as metallic medical devices. The coated devices may then be delivered to the locality where the nitric oxide is required. For example, a metal organic framework coated stent may be used to perform balloon angioplasty and the release of nitric oxide under these conditions may be used to reduce restenosis.

Typically, the metal organic frameworks are provided in a suitable form as discussed above, and then loaded with nitric oxide ready for storage under dry conditions and used at a later time.

A powdered metal organic framework loaded with nitric oxide may be used in topical applications such as for wound dressing, and may be provided in a bandage for application to a wound for release of the nitric oxide into the wound to aid healing. A metal organic framework provided as a monolith may be used e.g. for topical applications or, for example, for suppository application in the treatment of severe constipation.

According to a third aspect of the present invention, there is provided a metal organic framework material comprising releasably adsorbed nitric oxide for use in surgery and/or therapy.

According to a fourth aspect of the present invention, there is provided a pharmaceutical, neutraceutical or cosmetic preparation comprising a metal organic framework material comprising releasably adsorbed nitric oxide together with a pharmaceutical/neutraceutical/cosmetic carrier therefor.

In a fifth aspect, the present invention provides the use of a metal organic framework material comprising releasably adsorbed nitric oxide for the preparation of a medicament for use in the treatment or prophylaxis of disease.

Diseases or medical conditions which may be treated include infections of the skin, including dermatophyte fungi, leishmaniasis, molluscum and papilloma virus, and mycobacterium infections. Further uses include therapeutic applications in anti-neoplastic activities, immune response modification, treatment of Raynaud's disease, wound healing and skin pigment modification. Yet further uses include treatment of restenosis, psoriasis and eczema, and skin cancer (melanoma). Therapies for other bacterial problems include the reduction of severe foot or body odour problems, and in the treatment of Methicillin Resistant *Staphylococcus Aureus* infections.

According to a sixth aspect of the present invention there is provided a medical article comprising a metal organic framework material.

The metal organic framework material of the medical article may be provided without nitric oxide loaded therein to allow loading with nitric oxide prior to use and/or storage of the medical device ready for subsequent use.

Alternatively, the metal organic framework material of the medical article may be provided as a metal organic framework material comprising releasably adsorbed nitric oxide.

Suitable medical articles for use in the present invention include stents, catheters, wound dressings, bandages, self-adhesive plasters and patches.

The beneficial properties of nitric oxide may be advantageously employed in cosmetic and personal hygiene applications.

According to a seventh aspect of the present invention, there is provided use of a metal organic framework material comprising releasably adsorbed nitric oxide in cosmetic and/or personal hygiene applications.

For example the metal organic framework materials of the present invention which comprise releasably adsorbed nitric oxide may be used in cosmetic preparations; deodorants; skin preparations such as anti-aging skin preparations and preparations applied before, during or after hair removal by shaving or by application of depilatory preparations; hair preparations; depilatory preparations and the like.

Accordingly, the present invention also provides, as an eighth aspect, a cosmetic and/or personal hygiene product comprising a metal organic framework material which comprises releasably adsorbed nitric oxide.

The present invention also provides, as a ninth aspect, a method of releasing nitric oxide comprising the steps of
  (i) providing a metal organic framework material comprising releasably adsorbed nitric oxide;
  (ii) contacting said metal organic framework material with a medium into which said nitric oxide is to be released.

Such release of nitric oxide is preferably achieved in a controlled manner, for example, by providing a suitable metal organic framework material with an established controlled release profile.

The medium into which the nitric oxide is to be released may be simply air surrounding the nitric oxide loaded metal organic framework material, or may be, for example, an aqueous medium.

The release may be performed either inside an animal body, topically to an animal body or ex vivo in non-body applications such as release into cell cultures.

The release may be performed at any suitable temperature, however room or body temperature is preferred.

The method of releasing nitric oxide may be applied to the treatment of humans or animals and accordingly the present invention further provides as an tenth aspect a method of treatment or prophylaxis of an individual in need thereof comprising providing a metal organic framework material comprising releasably adsorbed nitric oxide and contacting said metal organic framework material with said individual.

The present invention also extends to the use of a metal organic framework material as described herein, for removing nitric oxide from a gas, for example a gas stream.

The present invention also extends to the use of a metal organic framework material as described herein, in combination with a de Nox catalyst, for removing nitric oxide from a gas, for example a gas stream.

For example, such uses may include nitric oxide removal from combustion engine exhaust gases.

Therefore, according to a tenth aspect of the present invention, there is provided a catalyst comprising a metal organic framework material.

The nitric oxide is typically removed though irreversible adsorption by the metal organic framework material.

The metal organic framework material is typically coordinatively activated as described herein.

The present invention also extends to novel metal organic framework materials.

In an eleventh aspect, the present invention provides a metal organic framework material of formula (I):

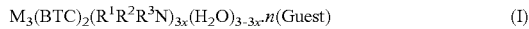

$$M_3(BTC)_2(R^1R^2R^3N)_{3x}(H_2O)_{3-3x}\cdot n(Guest) \quad (I)$$

wherein,

M is a divalent cation;

BTC is benzene tricarboxylate;

$R^1R^2R^3N$ is an amine where $R^1$, $R^2$ and $R^3$ are independently hydrogen or an organic group;

(Guest) is any number of independently selected species or molecules present in the pores of the material;

x is a variable from 0 to 1 in any ratio; and n is a variable from zero upwards.

Preferably, M is $Cu^{2+}$ or $Cr^{2+}$.

The organic group may be an alkyl group, such as a $C_1$-$C_{10}$, e.g. a $C_1$-$C_6$ alkyl group, such as independently methyl, ethyl, propyl, butyl or hexyl.

Preferably, each of $R^1$, $R^2$ and $R^3$ is hydrogen, in which case, the amine is ammonia.

Alternatively, one of $R^1$, $R^2$ and $R^3$, e.g $R^1$ is methyl, and the remaining two R groups (e.g. $R^2$ and $R^3$) are hydrogen, i.e. methyl amine.

The (Guest) species, in particular may be the amine $R^1R^2R^3N$, water or another component derived from the particular synthesis conditions used to provide the metal organic framework material, e.g. the solvent or part of the solvent.

Typically, the value of n is from 0 to 30.

For the avoidance of doubt, the values of x and n may not be whole numbers, but may be any incremental fraction between whole numbers.

The present invention in particular provides the material $Cu_3(BTC)_2(NH_3)_{3x}(H_2O)_{3-3x}\cdot n(Guest)$.

The values of n and x in the above materials, i.e., the amounts of amine, water and Guest species, become less on activation of the material in accordance with the principles described herein, and when fully activated, the values become zero, i.e. when all of the amine, water and Guest is removed from the material.

The present invention further provides in a twelfth aspect, a method of preparing a metal organic framework material of formula (I) comprising the steps of:

(i) providing and combining within a vessel a metal salt, a ligand compound, choline chloride and a urea; and (ii) heating the combined components of step (i) to provide the metal organic framework.

The method may provide further optional work-up steps, such as washing/purification steps following recovery of the framework material.

The ligand component is typically benzene tricarboxylate (BTC).

Preferably, the vessel is sealed, and may comprise any suitable material, e.g. glass.

Preferably, the combined components are heated by the action of microwaves.

Typically, the components are heated at a temperature of from about 50° C. to about 150° C., preferably about 100° C.

The components may be heated for the required period of time to provide the desired metal organic framework product. Typically, the components are heated for a period of time of from about 10 minutes to about 120 minutes, preferably from about 20 minutes to about 90 minutes, typically about 50 minutes.

It is observed that the choline chloride and urea components interact to provide a deep eutectic solvent mixture.

Advantageously, the amine species in the final metal organic framework material is derived from the urea component in the synthesis starting products.

Such urea may have the formula $R^4R^5NCONR^6R^7$, wherein $R^4$, $R^5$, $R^6$ and $R^7$ independently have the same meanings as previously described herein for $R^1$, $R^2$ and $R^3$.

Thus, ammonia (i.e. wherein each of the R groups in the general formula (I) is H) is provided by using an unsubstituted urea, i.e. $H_2NCONH_2$. As an alternative, methylamine, mentioned previously, may be provided by using a di-substituted urea of formula $H_3CHNCONHCH_3$. Still further, a metal organic framework material comprising both ammonia and methylamine species may be envisaged through the use of a mono-substituted urea such as $H_2NCONHCH_3$ or by using a mixture of unsubstituted and di-substituted ureas. Other numerous alternatives within the scope of the invention may be envisaged by the skilled practitioner.

In summary, the present invention thus provides metal organic frameworks which have excellent adsorption capacity for nitric oxide. The nitric oxide can be stored in the metal organic framework and the nitric oxide can be realeased, and thereby delivered, on contact with a suitable nucleophile.

The metal organic framework materials may also be used in combination with catalysts to remove and/or destroy unwanted nitric oxides (i.e. NOx compounds such as NO), as found in combustion gases.

The present invention is described with reference to the following non-limiting embodiments which exemplify the aspects of the present invention, together with the drawings.

EXAMPLES

Example 1

A New Metal Organic Framework, HKUST-EM, its Synthesis and No Adsorption Properties This is a new material synthesised using a eutectic mixture ionic liquids (Choline Chloride/urea) as both the solvent and the template. This is the first metal organic framework porous material to be prepared using this type of synthesis. The structure is similar in size and porosity to the CU(BTC) structure described below. However, the choline chloride/ urea eutectic mixture undergoes a decomposition reaction under the synthesis conditions and so the final material occludes $NH_3$, which markedly affects some of its properties (particularly its thermal and activation properties). Combined thermogravimetric and mass spectroscopic analysis indicates that the material contains $NH_3$ groups, and IR studies suggest that the $NH_3$ is bound to the metal ions. The overall composition of the material is $Cu_3(BTC)_2(NH_3)_{3x}(H_2O)_{3-3x}.n$ (Guest) where BTC=benzene tricarboxylate and Guest species are any molecules present in the pores of the as-synthesised structure ($H_2O$, $NH_3$, choline, unreacted benzenetricarboxylic acid, urea).

(a) Synthesis.

$Cu(NO_3)_2.4H_2O$ (380 mg, 1.5 mmol, Fisons), benzenetricarboxylic acid (210 mg, 1 mmol, Avocado), choline chloride (700 mg, 5 mmol) and urea (600 mg, 10 mmol) were sealed in a microwave-specified 5 mL glass tube and heated at 100° C. for 50 minutes (Biotage Initiator™, power range 0-300 W from magnetron at 2.45 G). Green tiny block crystals were collected, washed with methanol and dried in air. The crystals were too small for single crystal X-ray diffraction so characterisation was accomplished using powder X-ray diffraction.

(b) Activation Steps

Two methods of activation were tried, a thermal treatment and chemical treatment using several different species.

Thermal Treatment:

220c-1d: As-synthesized sample was heated at 220° C. for 24 hours. Their TGA and XRD patterns were recorded on cooling.

Sample Activation $CH_3CN$/DMF/EtOH/MeOH-1d:

The sample was stirred in $CH_3CN$ or DMF or EtOH or MeOH for 24 hours at room temperature. Their TGA and XRD patterns were recorded after filtering and drying in air.

(c) Analysis

Figure 1:
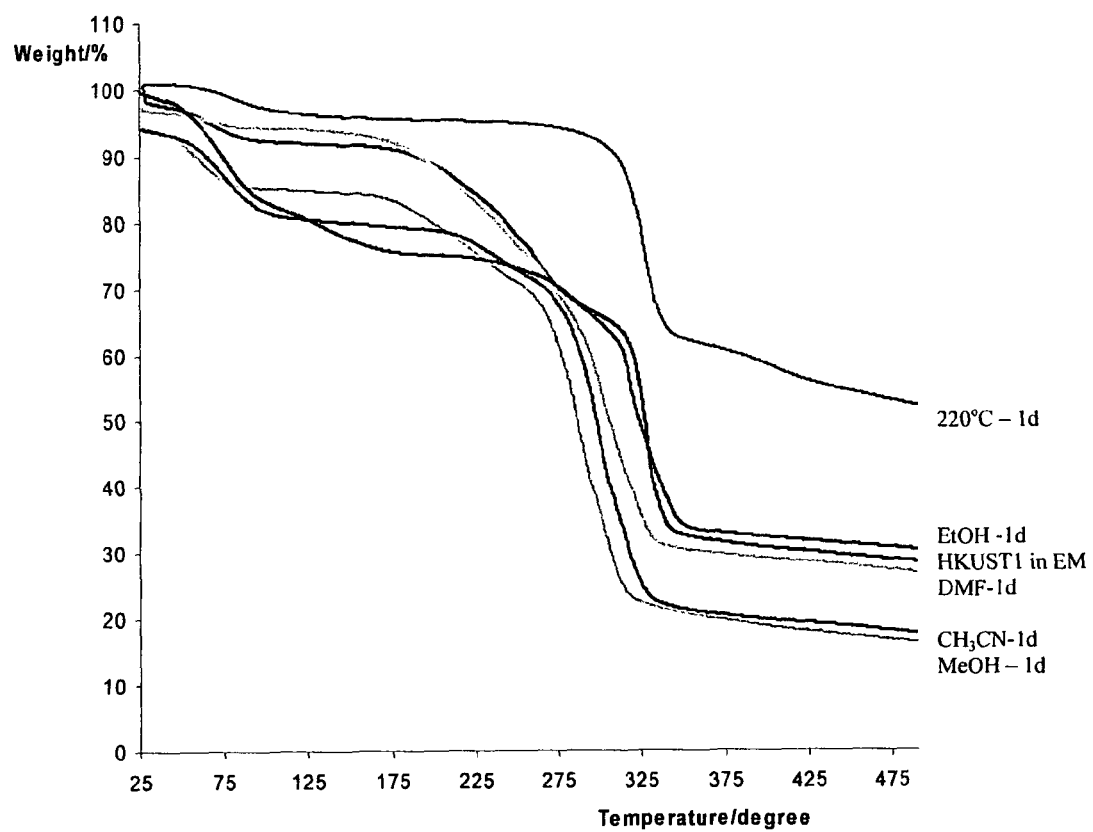
FIG. 1 shows the thermograivmetric analysis of HKUST1-EM before and after activation for 1 day. 220c-1d indicates thermal activation at 220° C. for 1 day. DMF-1d indicates chemical activation in dimethyl formamide (DMF) for 1 day.

The results of thermograivmetric analysis of HKUST1-EM before and after activation for 1 day are shown in FIG. 1.

Figure 2:
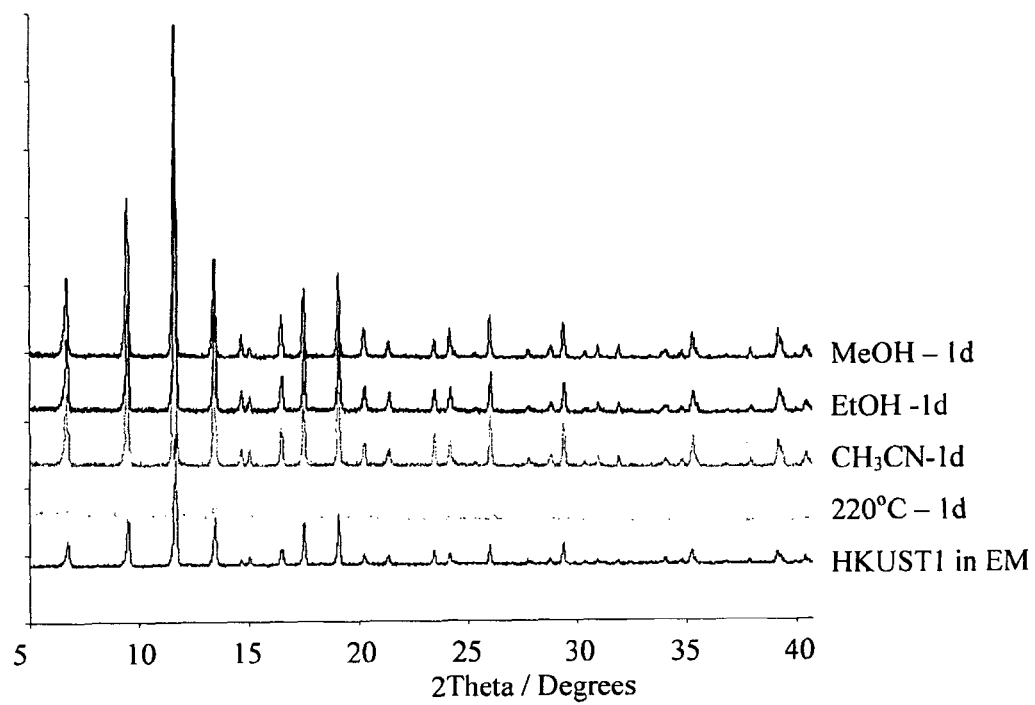
FIG. 2 shows X-ray diffraction of HKUST1-EM before and after activation, indicating that the structure of the solid essentially remains intact after removal of guest species.

The results of X-ray diffraction of HKUST1-EM before and after activation are shown in FIG. 2, indicating that the structure of the solid essentially remains intact after removal of guest species.

(d) NO Adsorption/Desorption

Figure 3:
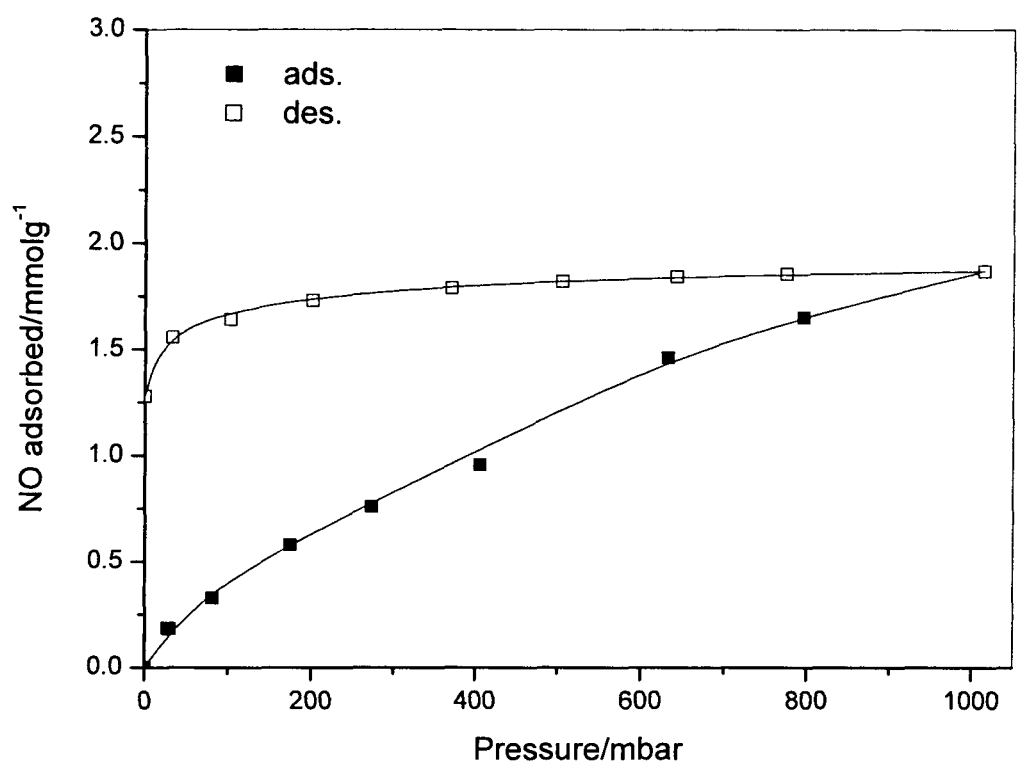
FIG. 3 shows the NO adsorption-desorption isotherm for HKUST1-EM after activation with methanol for 1 day—sample MeOH-1d (EM=eutectic mixture; 1d=1 day)

The adsorption/desorption of nitric oxide gas in HKUST1-EM was measured using a gravimetric adsorption system. The highest adsorption capacity for NO was shown by the material that had been activated by treatment for 1 day with methanol. A CI instruments microbalance was thermally stabilized to eliminate the effect from external environment. The microbalance has a sensitivity of 0.1 microgram and reproducibility of 0.01% of the load. ~100 mg of sample was initially outgassed at 383 K under 1×10-4 mbar for 24 hrs until no further weight loss was observed. The sample temperature was then decreased to 298 K and kept constant by a circulation water bath with temperature accuracy +−0.02 K. The counterbalance temperature was kept the same as that of the sample to minimize the influence of temperature difference on weight readings, and the sample temperature was monitored using a K type of thermocouple, located close to sample bucket (<5 mm). The variation in sample temperature was minimal (<0.2 K) throughout the experiment. NO gas was introduced into the system until the desired pressure was achieved, and the mass uptake of the sample was measured as a function of time. Each adsorption point was set to 20 hrs allowing adsorption equilibrium to achieve. In this manner an adsorption isotherm was collected by incrementally increasing the pressure and noting the mass gain of the sample at equilibrium. Desorption of nitric oxide gas adsorbed in the samples was performed by gradually decreasing the system pressure to a desired value (until 2×10-2 mbar). The results of the NO adsorption-desorption isotherm for HKUST1-EM after activation with methanol for 1 day—sample MeOH-1d are shown in FIG. 3.

Example 2

Adsorption of NO on Copper-1,3,5 Benzene Tricarboxylate (CuBTC) Metal Organic Frameworks (a) Synthesis of CuBTC ($Cu_3(BTC)_2(H_2O)_3$)

In a typical synthesis, 3.0 mmol of $Cu(NO_3)_2.3H_2O$ (0.716 g) and 2.0 mmol of benzene 1,3,5-tricarboxylic acid (0.421 g) was mixed with 12 ml of $EtOH/H_2O$ (50:50) solution in a Teflon-lined autoclave. The mixture was stirred for 30 mins at ambient temperature before heated. The autoclave was heated at 383 K for 24 hrs, and then cooled down to room temperature. The blue product was sonicated and washed by $EtOH/H_2O$ (50:50) solution, isolated by filtration and dried in air.

The crystalline nature of the product was identified using powder X-ray diffraction and the framework structure was found to be isostructural to the material HKUST-1 reported by Chui et al. (Science, 283, 1148-1150, 1999). However, gas adsorption experiments using nitrogen gas (77K) and carbon dioxide (273 K) indicated that the pore volume of this material was significantly greater than that reported by Chui and co-workers (pore volume up to 0.67 $cm^3 g^{-1}$).

(b) NO Adsorption/Desorption

Figure 4:
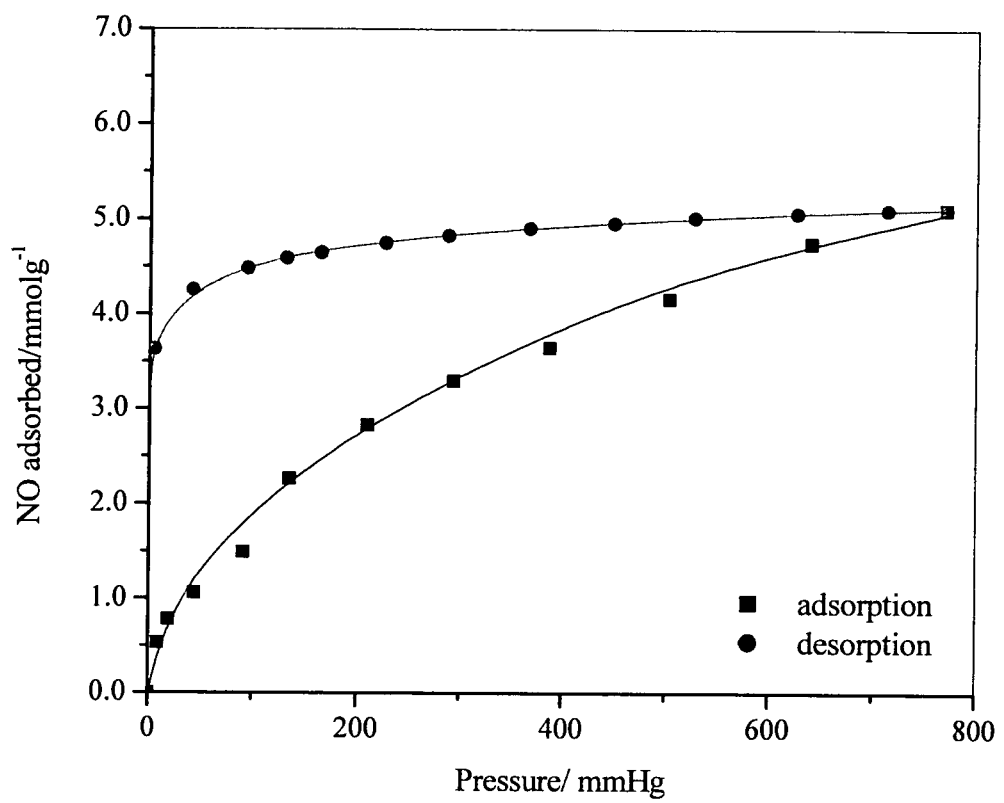
FIG. 4 shows the NO-adsorption desorption isotherm (298 K) for Cu-BTC.

The adsorption/desorption of nitric oxide gas in Cu-BTC was measured using a gravimetric adsorption system. A CI instruments microbalance was thermally stabilized to eliminate the effect from external environment. The microbalance has a sensitivity of 0.1 microgram and reproducibility of 0.01% of the load. ~100 mg of sample was initially outgassed at 383 K under $1\times10^{-4}$ mbar for 24 hrs until no further weight loss was observed. The sample temperature was then decreased to 298 K and kept constant by a circulation water bath with temperature accuracy +−0.02 K. The counterbalance temperature was kept the same as that of the sample to minimize the influence of temperature difference on weight readings, and the sample temperature was monitored using a K type of thermocouple, located close to sample bucket (<5 mm). The variation in sample temperature was minimal (<0.2 K) throughout the experiment. NO gas was introduced into the system until the desired pressure was achieved, and the mass uptake of the sample was measured as a function of time. Each adsorption point was set to 20 hrs allowing adsorption equilibrium to achieve. In this manner an adsorption isotherm was collected by incrementally increasing the pressure and noting the mass gain of the sample at equilibrium. Desorption of nitric oxide gas adsorbed in the samples was performed by gradually decreasing the system pressure to a desired value (until $2\times10^{-2}$ mbar). The results of the NO-adsorption desorption isotherm (298 K) for Cu-BTC are shown in FIG. 4. The adsorption isotherm shows strong NO uptake until a maximum of ~5 mmol NO per g of Cu-BTC is reached at ~800 mm Hg. The mass of the sample on desorption decreases only slightly on reduction of the NO pressure until around 22 mm Hg when the NO gas begins to desorb more fully. Even at the lowest pressure available ($2\times10^{-2}$ mbar) there is still evidence of significant residual NO on the material.

(c) Release of No on Contact with Water

Quantification of No Release by Chemiluminescence

Figure 5:
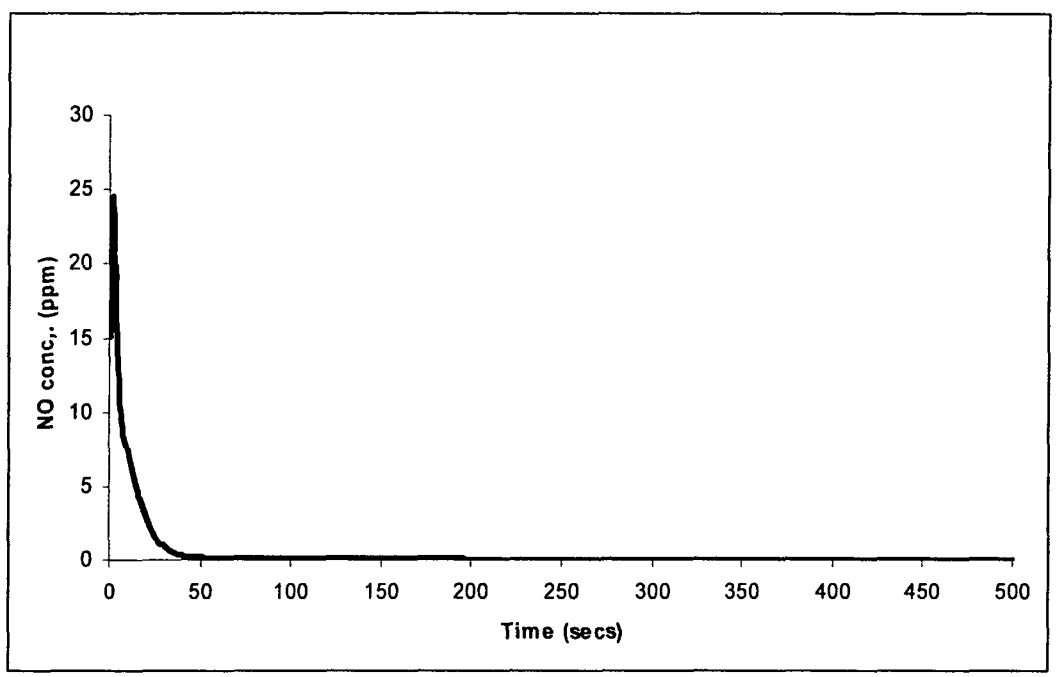
FIG. 5 shows the NO release profile for NO-loaded Cu-BTC in contact with water, measured using chemiluminescence.

NO measurements were performed using a Sievers NOA 280i chemiluminescence Nitric Oxide Analyzer. The instrument was calibrated by passing air through a zero filter (Sievers, <1 ppb NO) and 89.48 ppm NO gas (Air Products, balance nitrogen). The flow rate was set to 200 mL/min with a cell pressure of 8.5 torr and an oxygen pressure of 6.1 psig. To measure NO release from the MOF powder, nitrogen gas of known humidity was passed over the powders and the resultant gas was directed into the analyzer and the concentration of NO in ppm or ppb was recorded. The NO release profile, measured using chemiluminescence, for NO-loaded Cu-BTC in contact with water is shown in FIG. 5.

Example 3

Adsorption of NO on Chromium-1,3,5 Benzene Tricarboxylate (CrBTC) Metal Organic Frameworks (a) Synthesis of CrBTC $Cr_3F(H_2O)_2O(BTC)_3.nH_2O$ (where BTC=Benzene Tricarboxylate and n ~20-25)

In a typical synthesis metallic chromium (52 mg, 1 mmol) was added to an aqueous solution of 5 M hydrofluoric acid (0.4 mL, 2 mmol). After the addition of 1,3,5-benzene tricarboxylic acid $H_3BTC$ (150 mg, 0.67 mmol) and $H_2O$ (4.8 mL, $265\times10^{-3}$ mol), the mixture was heated in a Teflon-lined steel autoclave at 220° C. for 96 h. After cooling to room temperature the product was washed with deionized water and acetone and dried in air. The product was identified by powder X-ray diffraction as being isostructural with MIL-100 (Ferey et al, Angewandte Chemie International Edition, 43, 6296-6301, 2004).

(b) NO Adsorption/Desorption

The adsorption/desorption of nitric oxide gas in Cr-BTC was measured using a gravimetric adsorption system. A CI instruments microbalance was thermally stabilized to eliminate the effect from external environment. The microbalance has a sensitivity of 0.1 microgram and reproducibility of 0.01% of the load. ~100 mg of sample was initially outgassed at 383 K under $1\times10^{-4}$ mbar for 24 hrs until no further weight loss was observed. The sample temperature was then decreased to 298 K and kept constant by a circulation water bath with temperature accuracy +−0.02 K. The counterbalance temperature was kept the same as that of the sample to minimize the influence of temperature difference on weight readings, and the sample temperature was monitored using a K type of thermocouple, located close to sample bucket (<5 mm). The variation in sample temperature was minimal (<0.2 K) throughout the experiment. NO gas was introduced into the system until the desired pressure was achieved, and the mass uptake of the sample was measured as a function of time. Each adsorption point was set to 20 hrs allowing adsorption equilibrium to achieve. In this manner an adsorption isotherm was collected by incrementally increasing the pressure and noting the mass gain of the sample at equilibrium. Desorption of nitric oxide gas adsorbed in the samples was performed by gradually decreasing the system pressure to a desired value (until $2\times10^{-2}$ mbar).

Figure 6:
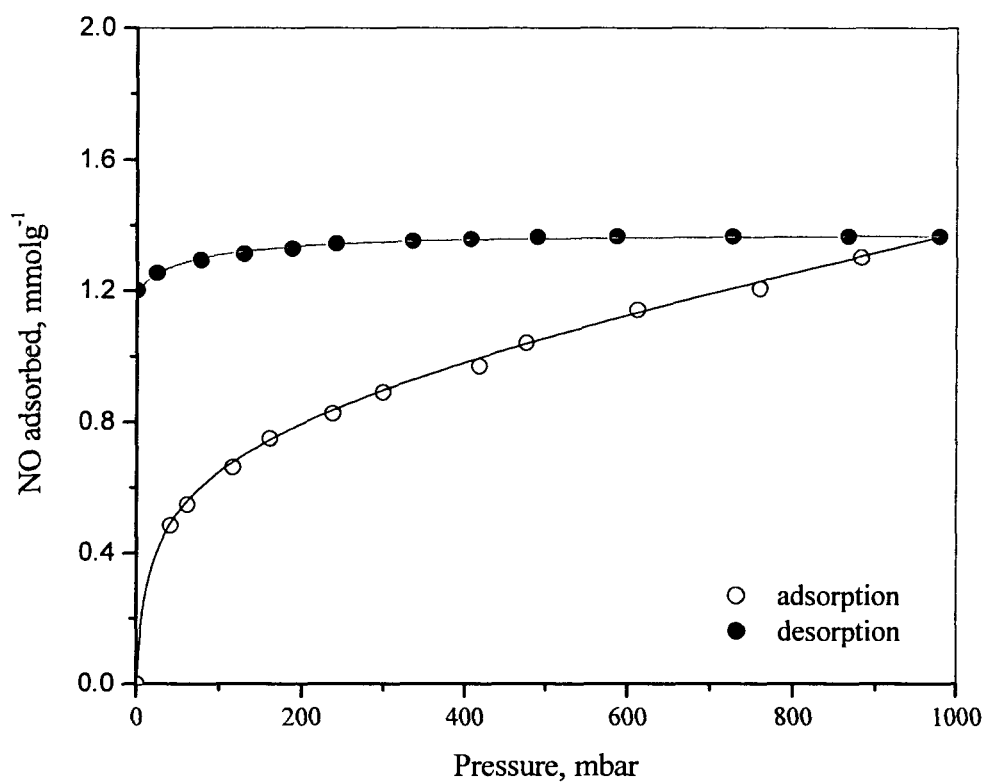
FIG. 6 shows the NO-adsorption desorption isotherm (298 K) for Cr-BTC.

The NO-adsorption desorption isotherm on Cr-BTC is shown in FIG. 6. The NO adsorption on Cr-BTC shows a hysteresis loop between adsorption and desorption. The amount of NO adsorbed at 298K and 1 atm is 1.37 mmolg$^{-1}$. This case indicated the stronger interaction of NO molecules with adsorption sites in Cr-BTC.

Example 4

NO Adsorption and Release from $M_2(dhtp)(H_2O)$ .$xH_2O$ (M=Ni or Co or Zn, dhtp=2,5-dihydroxy-terephthalic acid, x~8)

(a) Synthesis

Crystals of compound $M_2(dhtp)(H_2O).xH_2O$ (M=Co) of a suitable size for a single-crystal structure determination were obtained by reducing the molar ratio of cobalt acetate to ligand to 1:1. They were obtained by combining a solution of cobalt(II) acetate (187 mg, 0.75 mmol) in water (10 mL) and a solution of 2,5-dihydroxyterephthalic acid (149 mg, 0.75 mmol) in THF (10 mL) in a Teflon-lined steel autoclave and heating at 110° C. for three days. The crystals were isolated after filtration in 54% yield (95 mg, 0.2 mmol) with respect to cobalt.

The structure for the framework can be seen both with the excess water (before activation) and without (after dehydration). The activation of this compound requires only vacuum to remove the uncoordinated water in the sample (~29% mass), then heating to about 110° C. overnight to remove the remaining coordinated water to the metal (~7%). The Ni and Zn variants of the structure were made in an analogous fashion.

Figure 7:
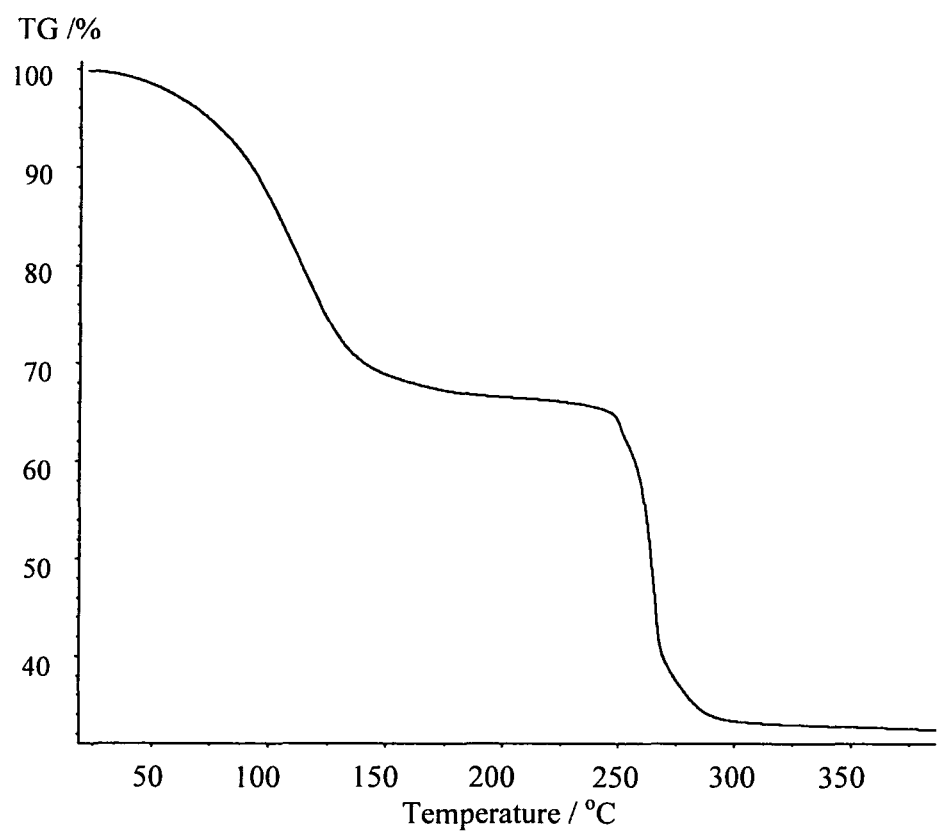
FIG. 7 shows Thermogravimetric analysis of $CO_2$(dhtp)($H_2O$)·$xH_2O$ (x~8)

A Powder X ray diffraction was carried out on $M_2(dhtp)(H_2O).xH_2O$ (M=Co) and the graph was a complete match for the published XRD pattern. Thermogravimetric analysis of $CO_2(dhtp)(H_2O).xH_2O(x~8)$ was also carried out and the results are shown in FIG. 7. The first mass loss can be attributed to water and possibly some excess 2,5-dihydroxyterephthalic acid still present in the framework but uncoordinated. The second mass loss is the destruction of the framework.

(b) NO Adsorption/Desorption Measurements.

The adsorption/desorption of NO gas in Co MOF was measured using a gravimetric adsorption system. A CI instruments microbalance was thermally stabilized to eliminate the effect from external environment. The microbalance has a sensitivity of 0.1 μg and reproducibility of 0.01% of the load. The pressure of the adsorption system was monitored by two BOC Edwards Active gauges in the ranges of $1 \times 10^{-8}$–$1 \times 10^{-2}$ and $1 \times 10^{-4}$–$1 \times 10^{3}$ mbar, respectively. The sample (~130 mg) was initially outgassed at 573 K under $1 \times 10^{-4}$ mbar, until no further weight loss was observed. The sample temperature was then decreased to 298 K and kept constant by a circulation water bath with temperature accuracy ±0.02 K. The counterbalance temperature was kept the same as that of the sample to minimize the influence of temperature difference on weight readings, and the sample temperature was monitored using a K type of thermocouple, located close to the sample bucket (<5 mm). The variation in sample temperature was minimal (<0.1 K) throughout the experiment. Nitric oxide gas was introduced into the adsorption system until the desired pressure was achieved, and the mass uptake of the sample was measured as a function of time until the adsorption equilibrium was achieved. In this manner an adsorption isotherm was collected by incrementally increasing the pressure and noting the mass gain of the sample after equilibrium was reached. The desorption of nitric oxide gas adsorbed in the samples was performed by gradually decreasing the system pressure to a desired value (until $2 \times 10^{-2}$ mbar).

(c) Quantification of NO Release by Chemiluminescence.

Nitric oxide measurements were performed using a Sievers NOA 280i chemiluminescence Nitric Oxide Analyzer. The instrument was calibrated by passing air through a zero filter (Sievers, <1 ppb NO) and 89.48 ppm NO gas (Air Products, balance nitrogen). The flow rate was set to 200 mL/min with a cell pressure of 8.5 Torr and an oxygen pressure of 6.1 psig. To measure NO release from Co MOF powders, nitrogen gas of known humidity was passed over the powders, the resultant gas was directed into the analyzer, and the concentration of NO in ppm or ppb was recorded.

Figure 8:
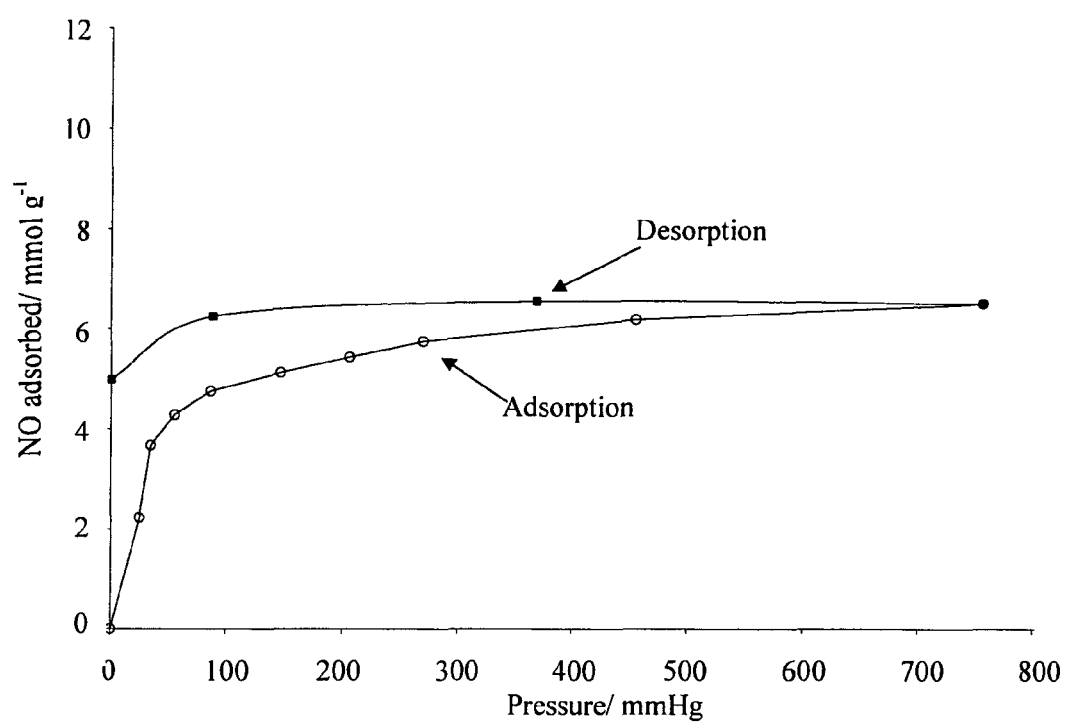
FIG. 8 shows The adsorption/desorption isotherm for $M_2(dhtp)(H_2O).xH_2O$ (M=Co)

The results of the adsorption/desorption isotherm for $M_2(dhtp)(H_2O).xH_2O$ (M=Co) are shown in FIG. 8.

As can be seen the Co compound acts like some of the zeolites that have previously been investigated (but they only absorbed 1.5 mmol/g). The Co MOF takes up over 6 mmol/g (i.e. 4 times as much as the best zeolites). The irreversibly adsorbed NO (i.e. that NO not released simply by reducing the pressure) is ~5 mmol/g of MOF, again significantly more than any other material yet prepared.

Figure 9:
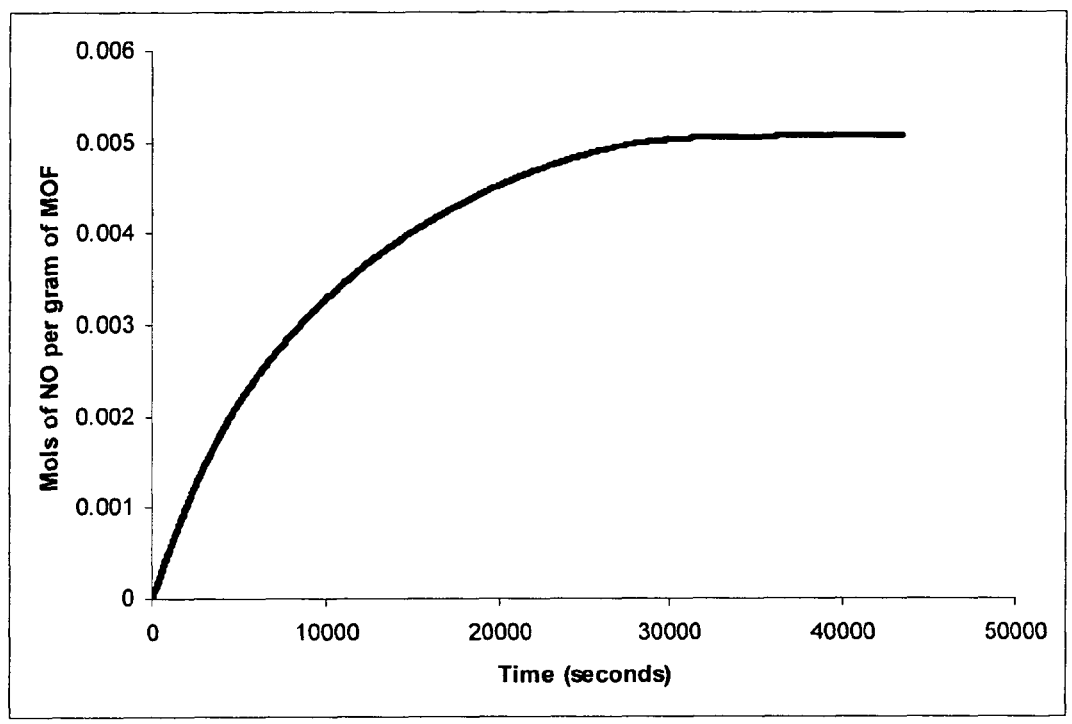
FIG. 9 shows Cumulative NO release profile for $M_2(dhtp)(H_2O).xH_2O$ (M=Co)

The delivery of NO on exposure to a trigger (in this case a controlled amount of water as described above) and measured using chemiluminescence can be seen in FIG. 9 which depicts the cumulative NO release profile for $M_2(dhtp)(H_2O).xH_2O$ (M=Co). The material is still releasing biologically significant amounts of NO after 30000 seconds. The results indicate that approximately 5 mmol/g are being released (i.e. all the irreversibly stored NO is releasable on contact with the water). This is once again significantly more than any other material yet published.

Figure 10:
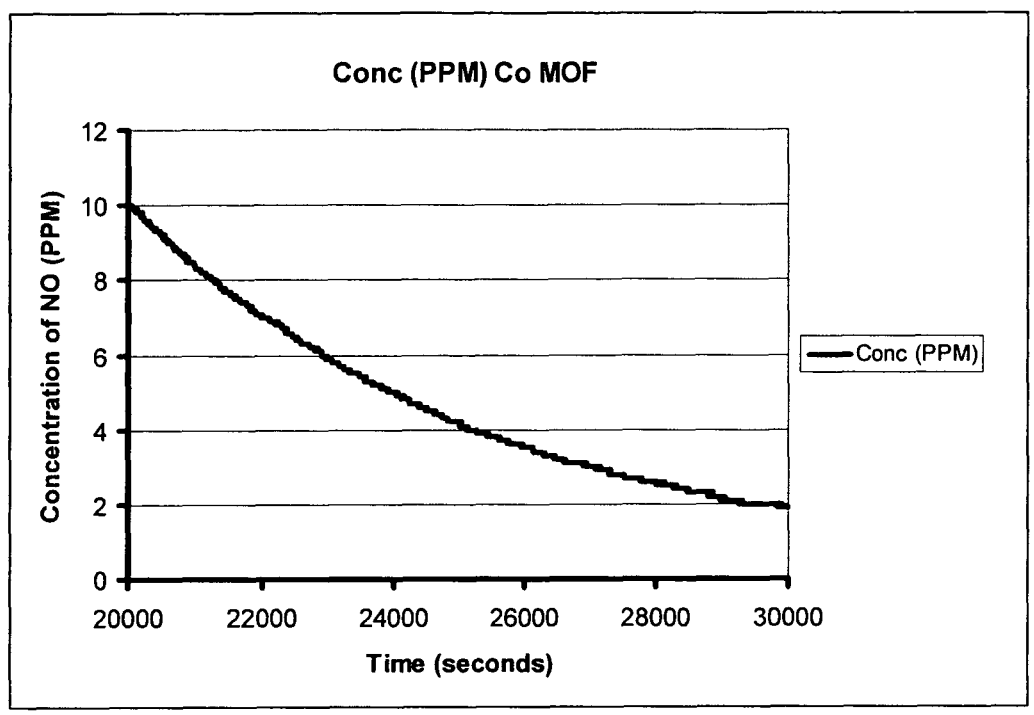
FIG. 10 shows The chemluminescence profile for $M_2(dhtp)(H_2O).xH_2O$ (M=Co)
Figure 11:
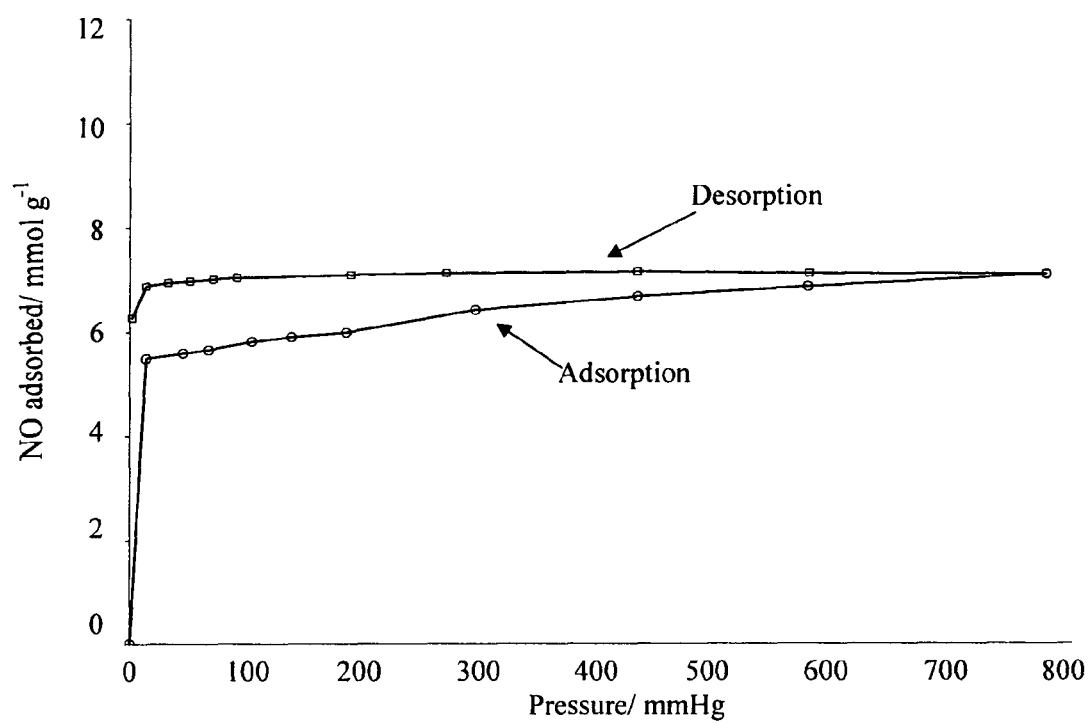
FIG. 11 shows The adsorption/desorption isotherm for $M_2(dhtp)(H_2O).xH_2O$ (M=Ni)

The Nickel compound $M_2(dhtp)(H_2O).xH_2O$ (M=Ni) adsorbs even slightly more NO, with a maximum adsorption capacity of >7 mmol/g and an irreversible adsorption capacity of >6 mmol/g (FIG. 10). The chemluminescence profile for $M_2(dhtp)(H_2O).xH_2O$ (M=Co) between 20000 and 30000 seconds after experiment began. The results shows the material is still giving off significant NO at 30000 seconds (~2 PPM under the cited conditions). After 337,000 seconds the reading on the chemiluminescence was still significantly above baseline (0.038 PPM). The release profiles of the NO delivered on exposure to moisture show that essentially all the 'irreversibly' adsorbed NO is delivered under these conditions (6 mmol/g) (see FIG. 11 which shows the adsorption/desorption isotherm for $M_2(dhtp)(H_2O).xH_2O$ (M=Ni)). This is the largest releasable capacity yet recorded for any material.

Figure 12:
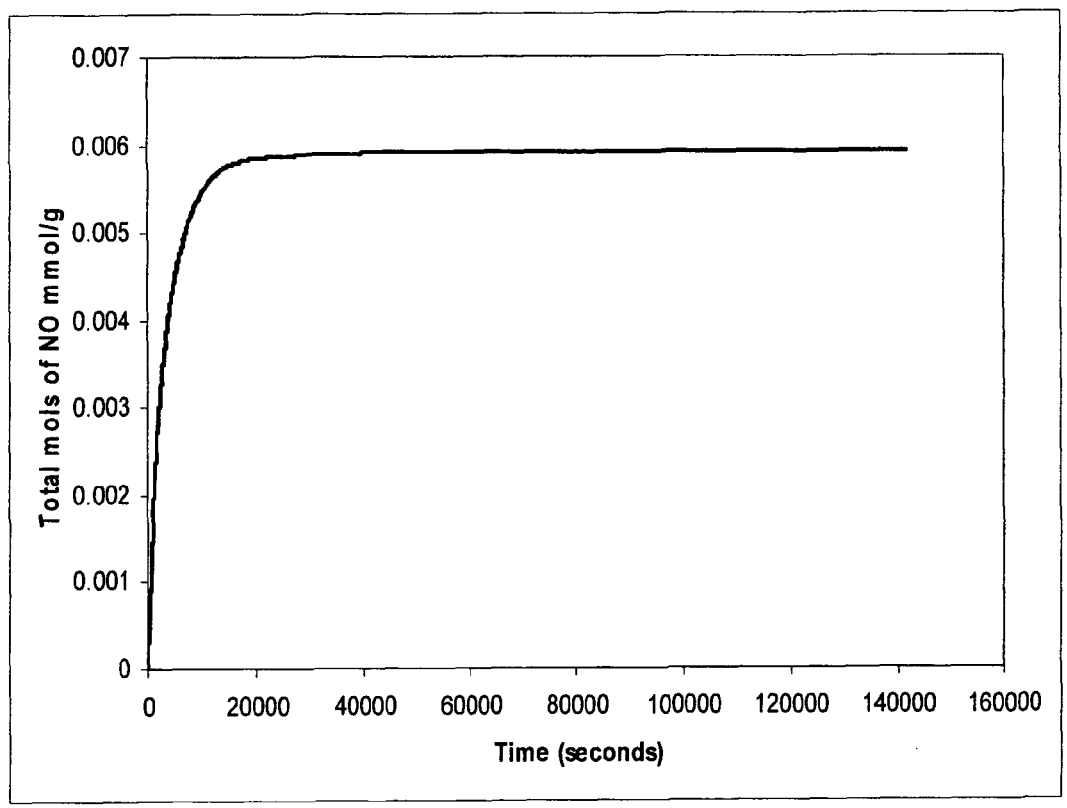
FIG. 12 shows The cumulative NO release profile measured by chemiluminescence for $M_2(dhtp)(H_2O).xH_2O$ (M=Ni)
Figure 13:
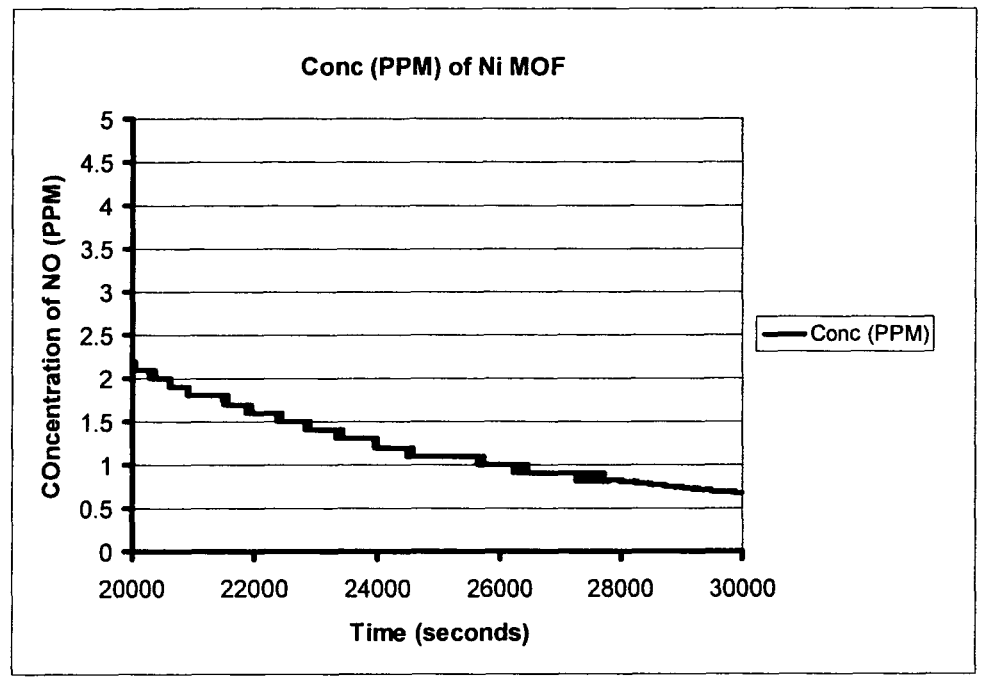
FIG. 13 shows The chemluminescence profile for $M_2(dhtp)(H_2O).xH_2O$ (M=Ni)

FIG. 12 shows the cumulative NO release profile measured by chemiluminescence for $M_2(dhtp)(H_2O).xH_2O$ (M=Ni) and FIG. 13 shows The chemluminescence profile for $M_2(dhtp)(H_2O).xH_2O$ (M=Ni) between 20000 and 30000 seconds after experiment began. The results shows the material is still giving off significant NO at 30000 seconds (~0.7 PPM under the cited conditions). After 141,500 seconds the reading on the chemiluminescence was still significantly above baseline (0.017 PPM).

For both the M=Co and M=Ni materials the NO is still being released at biologically relevant amounts between 30000 and 80000 seconds after the experiment began.

The results demonstrate that the NO adsorption capacities are extremely large for the materials, the releasable NO capacity here is very large (>5 times that of zeolites) and the release lasts a long time (the material is still releasing significant amounts of NO after 3-4 days under the experimental conditions).

Example 5

NO Adsorption and Release from CuSIP ($[Cu_2(OH)(SIP)(H_2O)].2H_2O$ where SIP=5-sulfoisophthalate).

Experimental

1. Syntheses of CuSIP

CuSIP: $[Cu_2(OH)(SIP)(H_2O)].2H_2O$

In a typical synthesis, $Cu(NO_3)_2.3H_2O$ (Alfa Aesar 98%) (2.42 g) and 5-sulfoisophthalic acid, sodium salt ($NaH_2SIP$) (Aldrich, 95%) (2.68 g) were dissolved in a 12 mL $EtOH/H_2O$ (50:50) solution. The mixture was heated in a 50 mL Teflon lined autoclave at 383K for five days, followed by naturally cooling down to room temperature. The yields were sonicated in a 100 mL $EtOH/H_2O$ solution for 5 minutes and then filtrated under vacuum. The aqua crystals were collected and dried in air.

2. Temperature Programming Desorption (TPD)

The temperature programming desorption (TPD) was carried out using a NETZSCH STA449C TG system connected to a PFEIFFER vacuum ThermoStar mass spectrometer through a quartz glass capillary heated at 453 K. ~10 mg sample was used for the TPD experiment. The sample was heated at rate of 5 $Kmin^{-1}$ in argon flow (45 $mLmin^{-1}$) until 1073K after the TG system was vacuumed three times and purged using dried argon gas (35 $mLmin^{-1}$). The species with m/z: 28 (CO), 44 ($CO_2$), 48 ($SO_2$) and 64 (SOA were monitored throughout experiment.

3. NO Adsorption/Desorption Isotherms

The isotherms of NO adsorption and desorption on samples were measured using a gravimetric adsorption system composed of a CI microbalance integrated with a thermal stabilizer, reactor, vacuum lines, thermostats and pressure transducers. The balance has sensitivity of 0.1 μg and reproducibility of 0.01% load. ~50 mg CuSIP were degassed under vacuum ($10^{-4}$ mbar) at 423K prior to NO adsorption until no further weight loss was observed. The dried NO gas (Air Liquide, 99.5%) was then introduced into the adsorption system. The isotherms of NO adsorption were obtained through controlling adsorption equilibrium at different desired pressures until up to 1 bar. Desorption was conducted by reducing NO pressure in adsorption system to the desired values until reaching equilibrium.

4. NO Storage Experiments

Samples were dehydrated at 423K under vacuo in vials for one day, followed by exposed to the dried NO gas (Air Liquide, 99.5%) at ~1 atm for 12 hours for NO storage. The vials with NO loaded samples were repeatedly evacuated and charged with argon three times and finally flame sealed.

5. Quantification of NO Release by Chemiluminescence

The NO stored in samples was released by passing nitrogen gas of given humidity through the sample bed with flow rate ~180 mL/min throughout measurement. The concentration of NO released was measured online using a Sievers NOA 280i chemiluminescence NO analyzer, operated at a cell pressure of 11.33 mbar and an oxygen pressure of 0.421 bar. The instrument was calibrated at zero NO gas and standard NO gas (89.48±0.9 ppm mol, Air Products) before NO release measurements.

Results

Figure 14:
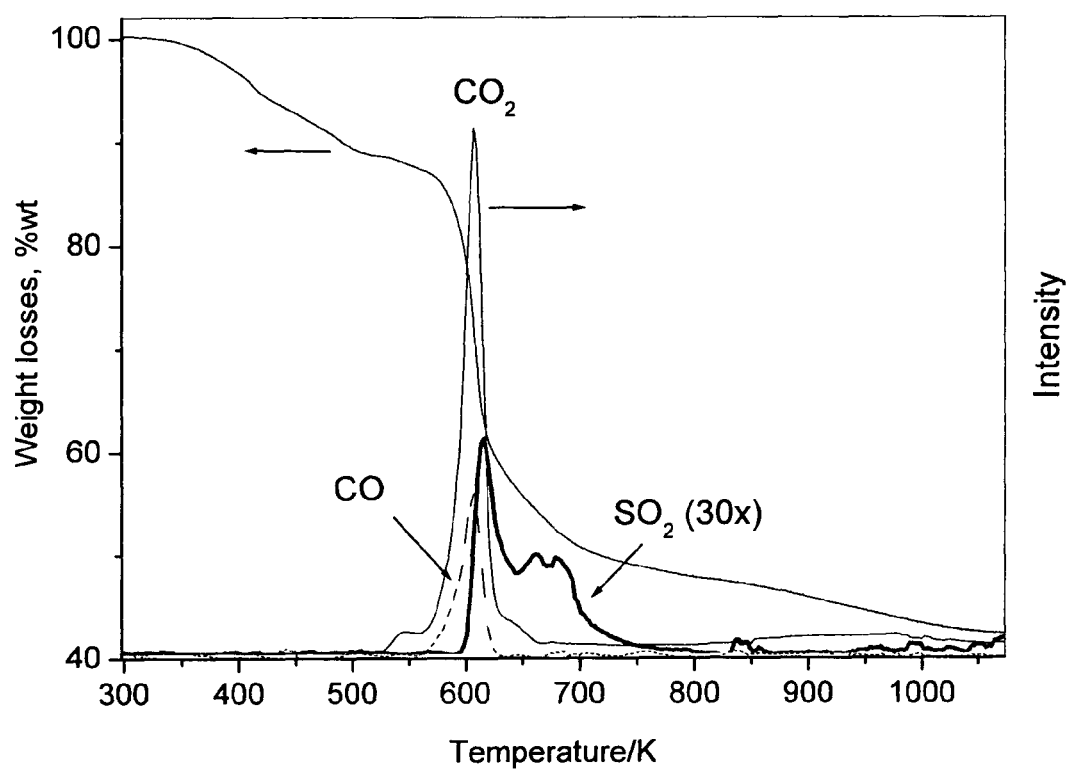
FIG. 14 shows The temperature programmed desorption of Cu-SIP.

1. Temperature Programmed Desorption of Cu-SIP (FIG. 14)

The first weight loss is 5.6% wt before 423K and the second is 5.38% wt in a range of 423-508K. Each weight loss is equivalent to 0.003 moles of water molecules per gram sample. CuSIP is decomposed beyond 560K to yield $CO_2$ and CO gas species from the —COO groups broken in a range of 570-670K. The —$SO_3$ groups bridged copper oxide clusters are broken in a wider range of 590-770K in the form of $SO_2$ released. $SO_3$ species were not detected throughout TPD experiment.

2. NO Adsorption/Desorption Isotherms (FIG. 15)

Figure 15:
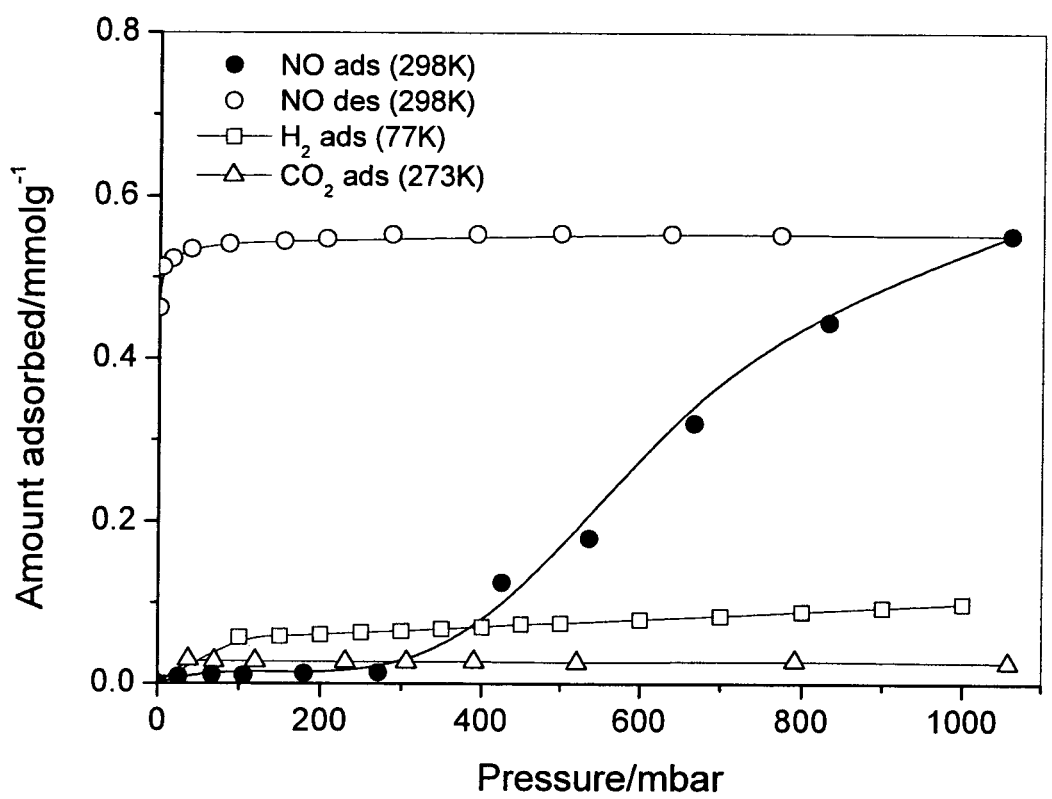
FIG. 15 shows NO, $H_2$ and $CO_2$ adsorption on CuSIP dehydrated at 423K.

FIG. 15 shows NO, $H_2$ and $CO_2$ adsorption on CuSIP dehydrated at 423K. This shows a novel gating mechanism for NO adsorption on CuSIP.

The amount adsorbed at ~1 bar is ~0.55 mmol/g. After desorption the residual NO remained ~0.46 mmol/g. The isotherm of NO adsorption showed little NO was adsorbed at low pressure<~270 mbar (the gating pressure). After that, NO begins to be gradually adsorbed on sample with pressure increasing until reaching ~0.55 mmol/g at ~1.06 bar. This type of isotherm is related to the so called 'gating' effect corresponding to crystal structure. There are no significant quantities of $N_2$(77K), CO (298K) or $CO_2$(298 K) adsorbed. The porosity determined by adsorption of $N_2$ and $CO_2$ is very low but the material has significant porosity when exposed to NO at greater than the gating pressure.

Figure 16:
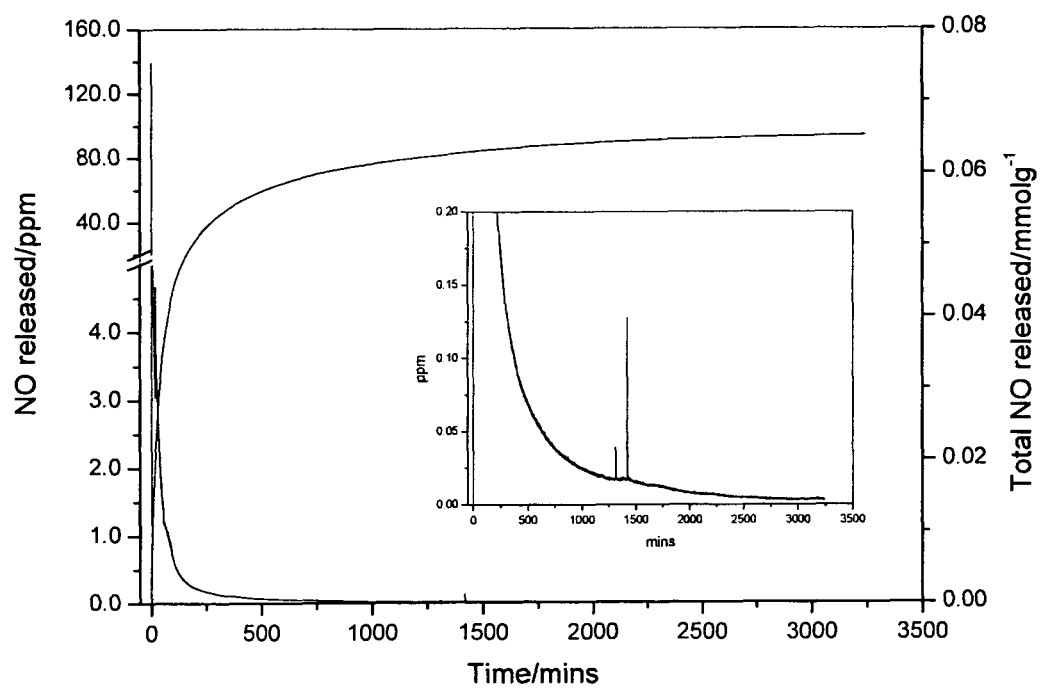
FIG. 16 shows NO release from CuSIP dehydrated at 423K.

3. NO Release from CuSIP Dehydrated at 423K (FIG. 16)

The quantity of NO released from sample CuSIP by water displacement was measured on line by Chemiluminescence method. The concentration of NO released from ~20 mg sample dropped from 140 ppm to 17 ppb after one day running, but still continues. The total quantity of NO released for two day running is about 0.065 mmolg$^{-1}$. The kinetic analysis of NO release showed that most of NO (62%) released with rate coefficient 4.4E-4 s$^{-1}$, the other with 3.3E-5 s$^{-1}$. These values are much lower than that of zeolites and HKUST-1, indicating NO release from the CuSIP materials take longer. It might be due to the slow diffusion of water into the locations of NO occupied or the gating effect also causing NO difficult to diffuse to outside of materials.

4. Crystal Structures

TABLE 1

Crystallographic data[a] for CuSIP (1)

|  | 1 |
|---|---|
| Formula | $C_8H_{10}Cu_2O_{11}S$ |
| FW | 441 |
| T/K | 293 |
| Crystal system | Monoclinic |
| Space group | P21/n |
| V/Å$^3$ | 1337.53(15) |
| Z | 4 |
| a/Å | 7.2806(5) |
| b/Å | 18.2421(11) |
| c/Å | 10.1075(6) |
| α/deg |  |
| β/deg | 94.8860(10) |
| γ/deg |  |
| Reflection collected | 14565 |
| Independent reflections | 3998 |
| Reflections observed | 3140 |
| R(int) | 0.0739 |
| Final R [I > 2σ(I)] | 0.0417 |
| Final w$R_2$ | 0.0989 |

[a]obtained with synchrotron radiation (λ = 0.69110 Å) for 1.

(1) [$Cu_2$(OH)(SIP)($H_2O$)].2$H_2O$

Figure 17:
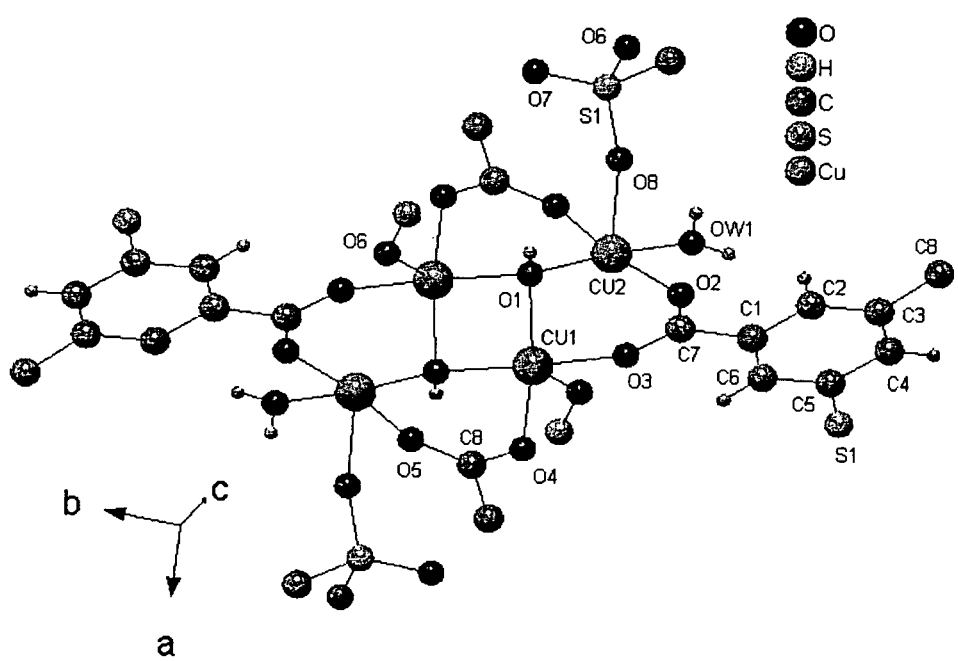
FIG. 17 shows view of the Cu-SIP structure showing various views and sizes of channels in the as made material and FIGS. 18a, 18b, 19a, 19b, 20a and 20b show views of the Cu-SIP structure showing various views and sizes of channels in the as made material.

The crystal structure of CuSIP shows that the material is essentially non-porous in the as made state. However, as shown in FIG. 17, there are water molecules (Ow1) that can be removed to provide a coordination site for the NO (a so-called accessible or open metal site). Since NO is a relatively strongly coordinating gas, at the gating pressure there is enough NO to coordinate to the copper and the flexibility of the structure itself then allows the material to open up and take in more NO. This coordination-driven gating process is novel as far as we are aware. The combination of selectivity to NO with this unusual adsorption mechanism makes this material of very great interest.

Figure 18A:
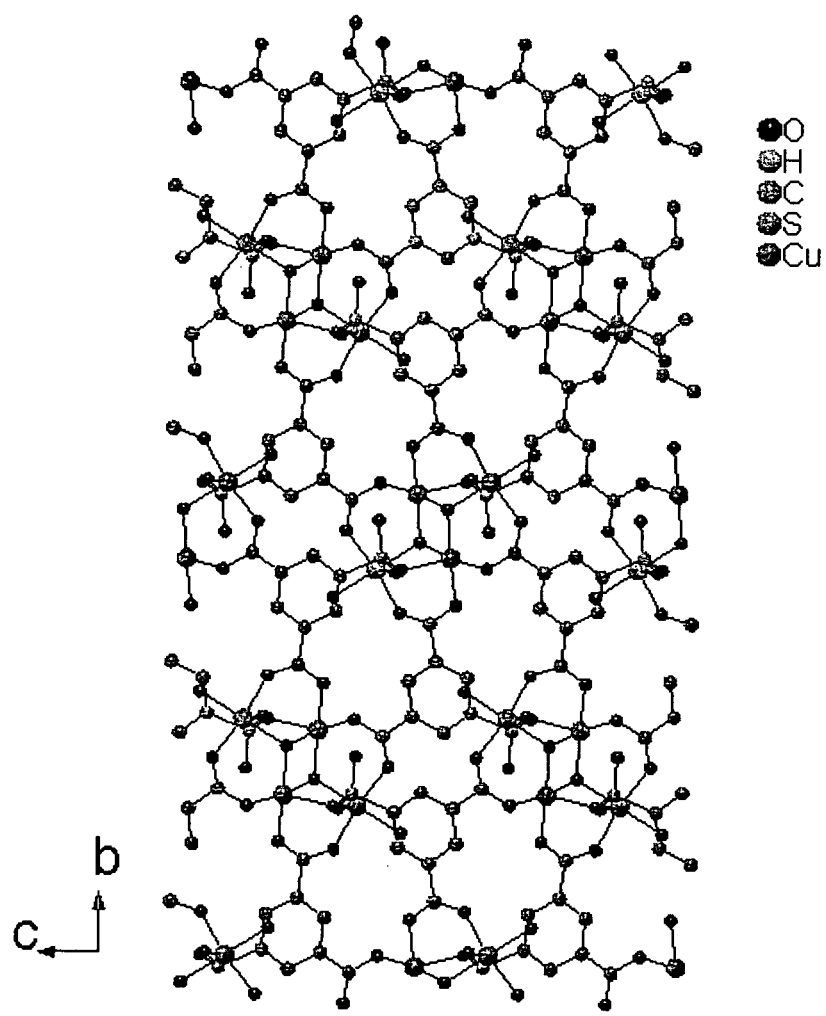
Figure 18B:
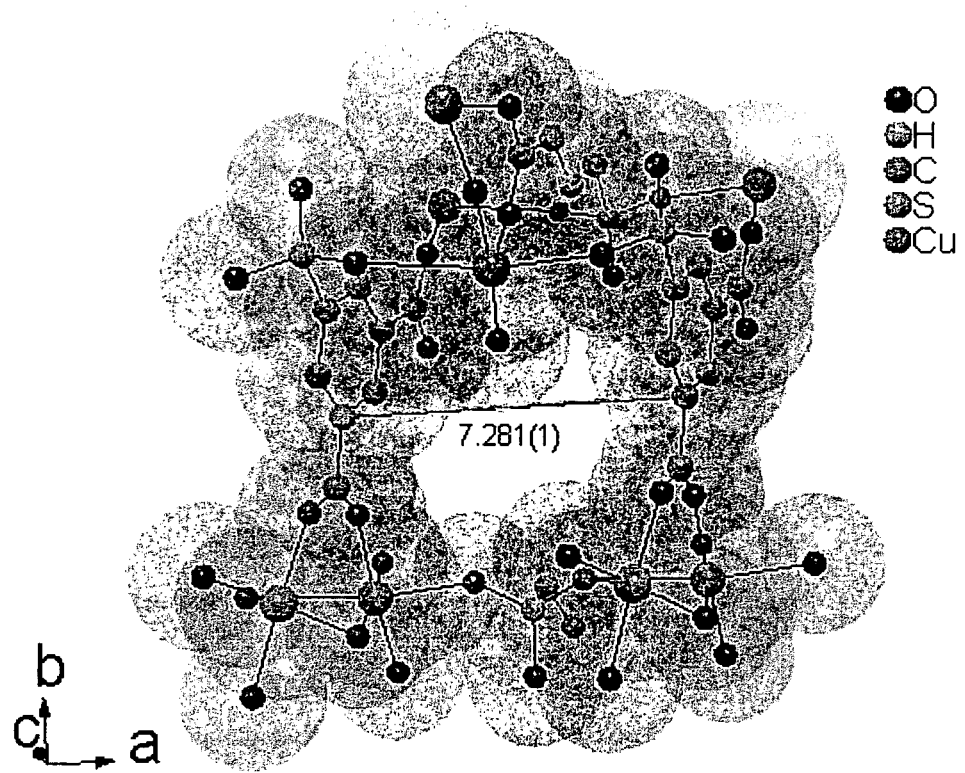
Figure 19A:
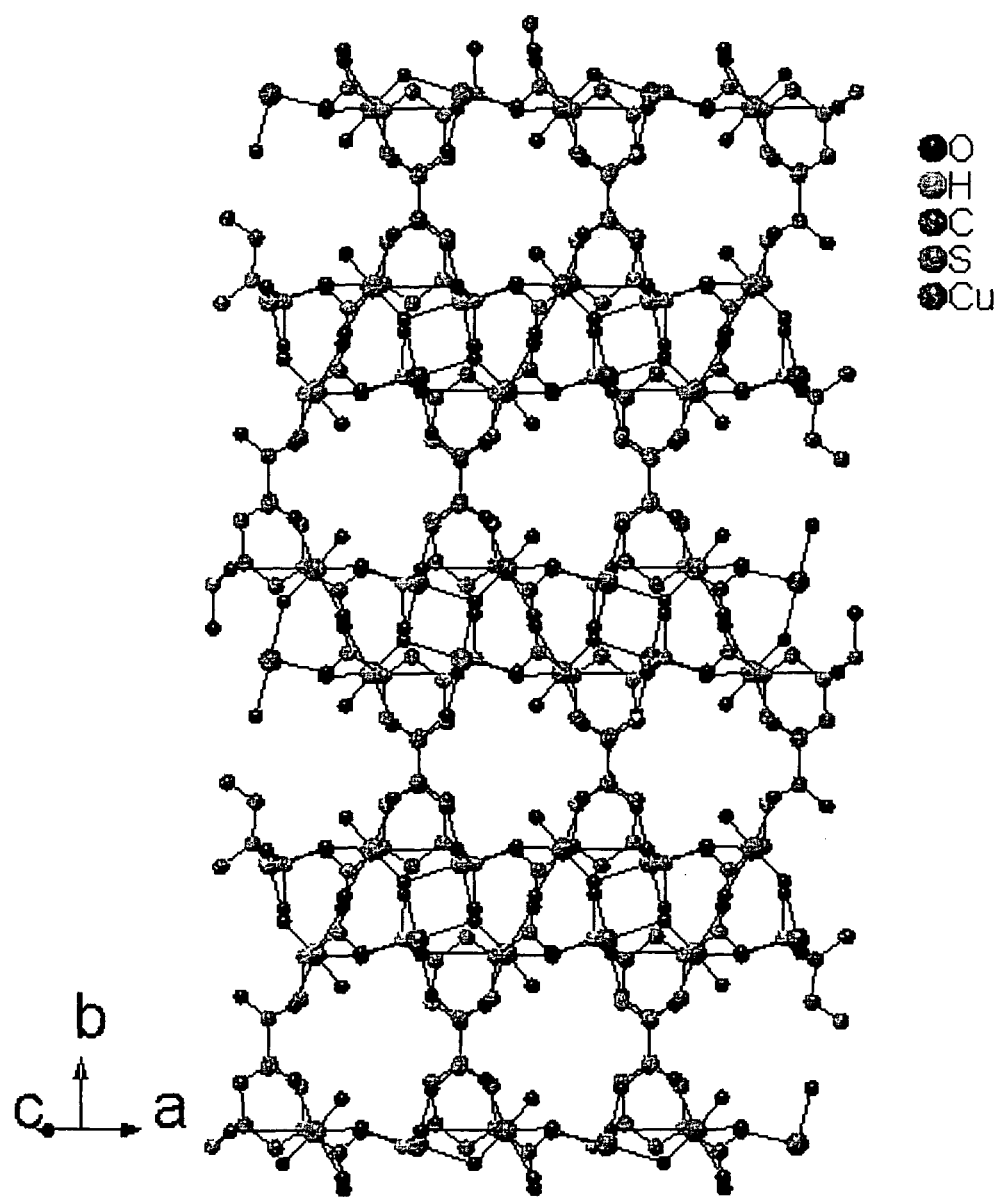
Figure 19B:
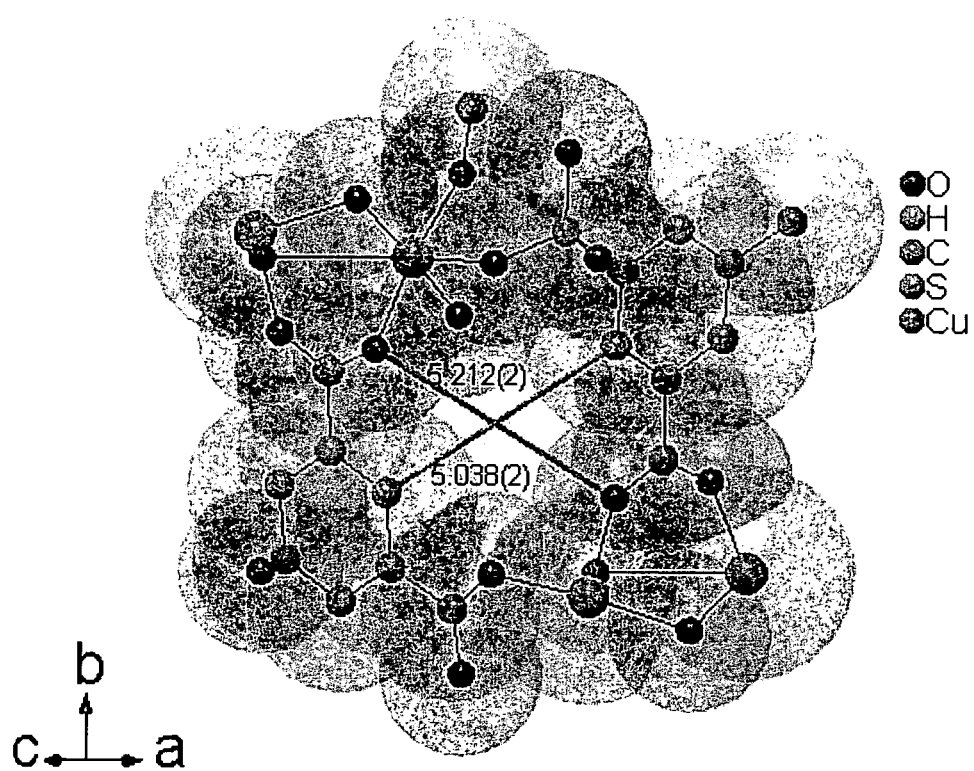
Figure 20A:
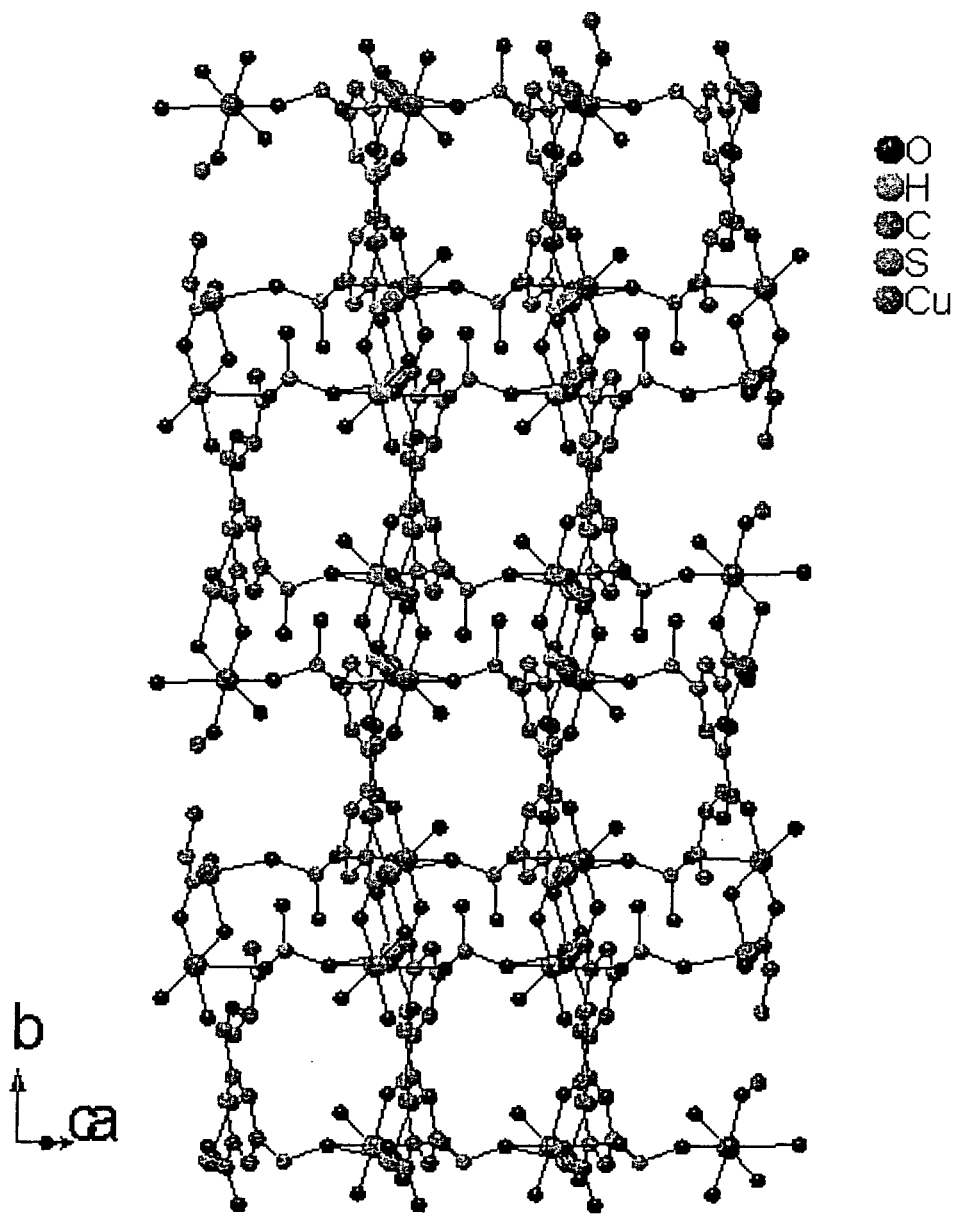
Figure 20B:
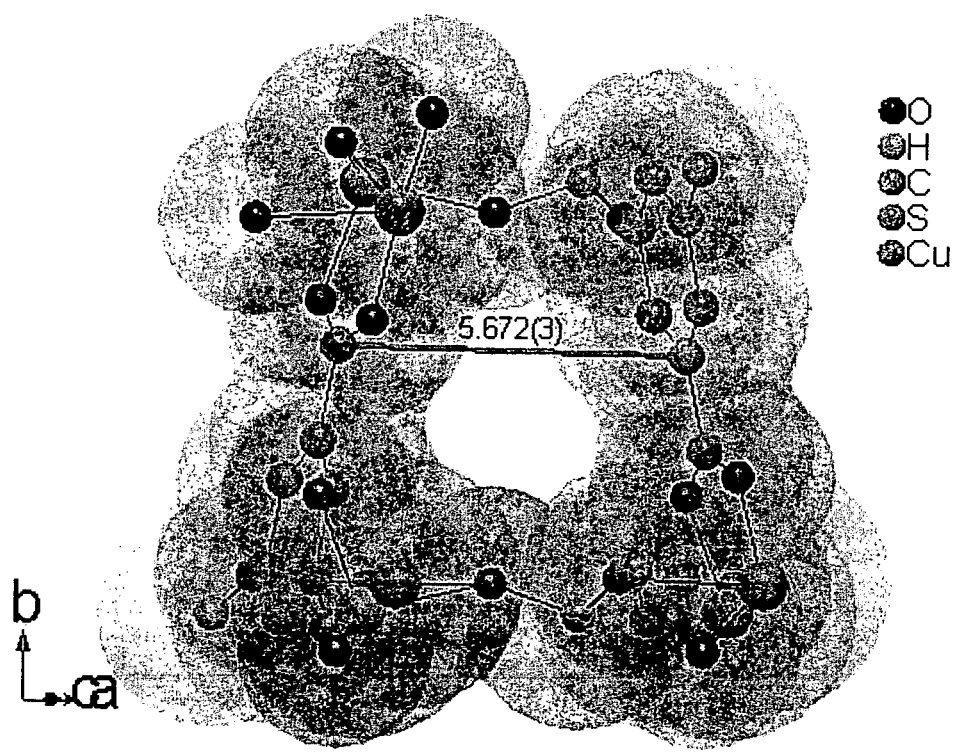

FIGS. 18a,b-20a,b show different views of the Cu-SIP structure showing various views and sizes of channels in the as made material.

The experiments indicate that:
1. CuSIP is a novel solid;
2. The CuSIP material is extremely selective for adsorption of NO after the correct activation treatment. None of the other gases tried were adsorbed;
3. The adsorption mechanism of NO on Cu-SIP is a novel coordination driven gating process.

The foregoing examples are provided as non-limiting illustrative embodiments of the present invention, which is not to be considered as limited thereby.

The invention claimed is:

1. A metal organic framework comprising adsorbed gaseous nitric oxide, wherein the metal organic framework comprises a three dimensional network in which metal ions are linked together with ligand linkers (L).

2. The metal organic framework according to claim 1, wherein the metal ions comprise metal cations selected from the group consisting of transition metal cations, alkali metal cations, alkaline earth metal cations, aluminium cations, and mixtures thereof.

3. The metal organic framework according to claim 2, wherein the transition metal cations are selected from the group consisting of one or more of: $Ti^{n+}$, $V^{n+}$, $Cr^{n+}$, $Mn^{n+}$, $Fe^{n+}$, $Co^{n+}$, $Ni^{n+}$, $Cu^{n+}$, $Zn^{n+}$, $Ag^{n+}$, $Ru^{n+}$, $Rh^{n+}$, where n is 1, 2, 3 or 4.

4. The metal organic framework according to claim 3, wherein the transition metal cations are selected from the group consisting of $Cu^+$, $Cu^{2+}$, $Cr^{2+}$, $Zn^{2+}$, $Fe^{2+}$, $Fe^{3+}$, $Co^{2+}$, $Co^{3+}$, $Ag^+$, $Mn^{2+}$ and $Mn^{3+}$ and mixtures thereof.

5. The metal organic framework according to claim 2, wherein the alkali metal cations include $Na^+$ and $K^+$, and the alkaline earth metal cations include $Ca^{2+}$ and $Mg^{2+}$.

6. The metal organic framework according to claim 1, wherein the ligand linkers (L) comprise organic compounds containing multiple coordinating atoms, coordinating sites or functional groups.

7. The metal organic framework according to claim 6, wherein each ligand linker L includes from 2-10 coordinating sites.

8. The metal organic framework according to claim 6, wherein the coordinating site comprises an electron donating moiety, a negative charge, or atoms or groups capable of forming such moieties.

9. The metal organic framework according to claim 6, wherein each ligand linker is a dentate ligand selected from bidentate and tridentate ligands.

10. The metal organic framework according to claim 6, wherein the ligand linkers are selected from carboxylate ligands and amine ligands.

11. The metal organic framework according to claim 10, wherein the carboxylate ligands are selected from 1,4-benzene-dicarboxylic acid, 1,3,5-benzene tricarboxylic acid and 5-sulfoisophthalic acid.

12. The metal organic framework according to claim 10, wherein the amine ligand is 1,4-bipyridine.

13. The metal organic framework according to claim 1 additionally comprising anions selected from halides, $OH^-$ or $SO_4^-$.

14. The metal organic framework according to claim 1, which is sealed inside airtight packaging.

15. The metal organic framework according to claim 1, in the form of a powder or monolith.

16. The metal organic framework according to claim 15, wherein the monolith (i) is formed by compression of a metal organic framework powder or (ii) further comprises a binder and is formed by mixing a powdered metal organic framework with the binder.

17. The metal organic framework according to claim 16, wherein the binder is selected from the group consisting of ceramic binders, polymeric binders and other polymers.

18. A method of preparing a metal organic framework of claim 1, said method comprising the steps of providing said metal organic framework comprising a three dimensional network in which metal ions are linked together with ligand linkers (L) and contacting said metal organic framework with gaseous nitric oxide.

19. The method according to claim 18, wherein, prior to contact with the gaseous nitric oxide, the metal organic framework is fully or partially activated by removing guest molecules or species from interior pores and/or channels of the framework to allow the nitric oxide to be adsorbed into the metal organic framework.

20. The method according to claim 19, wherein activation of the metal organic framework is achieved chemically, optionally followed by other non-chemical means or vice versa.

21. The method according to claim 20, wherein the chemical activation removes guest molecules from the framework by chemical displacement of the guest molecules by the molecules of the activating chemical species.

22. The method according to claim 20, wherein the non-chemical means for activation comprises heating the metal organic framework at atmospheric or reduced pressure, or subjecting the framework material to reduced pressure in absence of heat.

23. The method according to claim 21, wherein the activating chemical species comprises a solvent selected from the group consisting of acetonitrile ($CH_3CN$), dimethylformamide (DMF), ethanol (EtOH) and methanol (MeOH).

24. The method according to claim 18, wherein the guest molecules comprise water so that activation of the framework includes full or partial dehydration of the framework material.

25. The method according to claim 18, wherein the metal organic material is contacted with nitric oxide at a temperature of from $-100°$ C. to $50°$ C.

26. The method according to claim 18, wherein the nitric oxide is provided as substantially pure nitric oxide gas or as a mixture of nitric oxide gas and a carrier gas.

27. The method according to claim 26, wherein the carrier gas is an inert gas chosen from helium, argon or other inert gas including mixtures thereof.

28. The method according to claim 18, wherein the metal organic framework is contacted with nitric oxide gas at a pressure of from about atmospheric pressure up to a pressure of about 10 bar.

* * * * *